United States Patent

Scaringe et al.

[11] Patent Number: 6,008,400
[45] Date of Patent: Dec. 28, 1999

[54] ORTHOESTER REAGENTS FOR USE AS PROTECTING GROUPS IN OLIGONUCLEOTIDE SYNTHESIS

[76] Inventors: Stephen Scaringe, 5530 Stonewall Pl.; Marvin H. Caruthers, 2450 Cragmoor Rd., both of Boulder, Colo. 80303

[21] Appl. No.: 08/994,824

[22] Filed: Dec. 19, 1997

Related U.S. Application Data

[62] Division of application No. 08/488,878, Jun. 9, 1995.

[51] Int. Cl.$^6$ .................. C07C 255/11; C07C 255/49; C07C 43/30; C07C 43/32
[52] U.S. Cl. .................. 558/423; 558/435; 568/595; 568/597; 568/598; 568/614
[58] Field of Search .................. 558/423, 435; 568/595, 597, 598, 614

[56] References Cited

U.S. PATENT DOCUMENTS

| | | |
|---|---|---|
| 4,415,732 | 11/1983 | Caruthers et al. . |
| 4,458,066 | 7/1984 | Caruthers et al. . |
| 4,999,428 | 3/1991 | Saksena et al. . |
| 5,015,739 | 5/1991 | Saksena et al. . |

FOREIGN PATENT DOCUMENTS 9641809  12/1996  WIPO .

*Primary Examiner*—Johann Richter
*Assistant Examiner*—Taofiq A. Solola

[57] ABSTRACT

Phosphoramidite oligonucleotide synthesis is facilitated by the use of fluoride-labile 5' silyl protecting groups. RNA synthesis is improved by the use of 2 orthoester protecting groups. Reactions are conducted on a solid phase support and acidic deprotection conditions are avoided, as is the necessity of oxidizing the phosphite linkage between each coupling reaction.

15 Claims, 16 Drawing Sheets

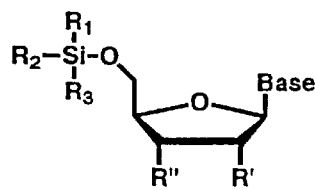
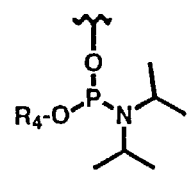
(I)   (Ia)
Where $R_1$, $R_2$, $R_3$ =
    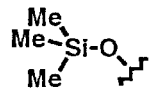
a     b     c     d     e
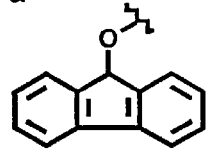 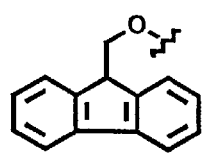 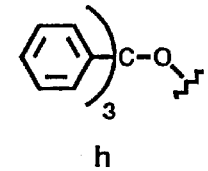
f     g     h
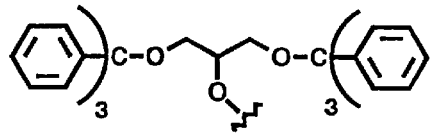 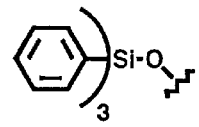 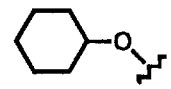
i     j     k
Figure 1
| I - R1, R2, R3 | $t_{complete}$ w/ 5eq. TBAF/THF |
|---|---|
| I-a,a,b | <1 min |
| I-a,a,h | <15 sec |
| I-a,a,j | <15 sec |
| I-a,a,f | <30 sec |
| I-a,a,g | <30 sec |
| I-a,b,b | <30 sec |
| I-b,b,b | <15 sec |
| I-b,b,j | <15 sec |
| I-d,j,j | <15 sec |
| I-j,k,k | <15 sec |
| I-d,e,e | <15 sec |
| I-j,j,k | <15 sec |
| I-e,e,e | <15 sec |
| I-e,e,k | <15 sec |
| I-e,k,k | <15 sec |
| I-k,k,k | <15 sec |
| I-i,e,e | <15 sec |
Figure 1(A)

DNA/RNA 5'-Silyl Synthesis Cycle

| Compound | 1/2 life at pH 2.0 (min.) |
| --- | --- |
| II-L | 6.4 |
| II-M | 133 |
| II-N | 1.1 |
| II-O | 1.2 |
| II-P | 44 |
| II-Q | ~4.0 |
| II-S | ~13.9 |
| II-T | 7.5 |
| II-U | 1.8 |
| II-V | 2.8 |
| II-W | 5.7 |
| II-X | 35.4 |

Prior Art

Prior Art i.) Unblock the 5' group
ii.) Couple the 5' unblocked end with second base
iii.) Any 5' ends that did not react (~<2%) are capped
iv.) Stabilize linkage between base one and base two
i.) Chain is now two bases long - unblock 5' end and repeat cycle to add base three

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 5 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:1:

TTTTT                                                                 5

(2) INFORMATION FOR SEQ ID NO:2:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:2:

AAAAAAAAAT                                                  10

(2) INFORMATION FOR SEQ ID NO:3:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: RNA (synthetic)

(xi) SEQUENCE DESCRIPTION: SEQ ID NO:3:

AAAAAAAAAT                                                10

(2) INFORMATION FOR SEQ ID NO:4:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: RNA (synthetic)

(xi) SEQUENCE DESCRIPTION: SEQ ID NO:4:

CCCCCCCCCT                                                10

(2) INFORMATION FOR SEQ ID NO:5:

(i) SEQUENCE CHARACTERISTICS:
      (A) LENGTH: 10 base pairs
      (B) TYPE: nucleic acid

```
        (C) STRANDEDNESS: single
        (D) TOPOLOGY: linear (ii) MOLECULE TYPE: RNA (synthetic)

(xi) SEQUENCE DESCRIPTION: SEQ ID NO:5:

UUUUUUUUUT                                                              10

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: RNA (synthetic)

(xi) SEQUENCE DESCRIPTION: SEQ ID NO:6:

GAAUCGAAAC GCGAAAGCGU ACUAGCGT                                          28

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: RNA (synthetic)

(xi) SEQUENCE DESCRIPTION: SEQ ID NO:7:

CUUAGAGUAG UCAUCGCT                                                     18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: RNA (synthetic)

(xi) SEQUENCE DESCRIPTION: SEQ ID NO:8:

UUUAGAGUAG UUAUUGUT                                                     18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: RNA (synthetic)

(xi) SEQUENCE DESCRIPTION: SEQ ID NO:9:

CGCUACUGAU GAGAUUCT                                                     18
```

ORTHOESTER REAGENTS FOR USE AS PROTECTING GROUPS IN OLIGONUCLEOTIDE SYNTHESIS

This application is a division of application Ser. No. 08/488,878, filed Jun. 9, 1995.

SEQUENCE LISTING

This application is accompanied by a sequence listing in printed form as well as a computer-readable form that identically replicates the contents of the printed form.

BACKGROUND OF THE INVENTION

1. Field of the Invention

The present invention pertains to the field of protecting groups in organic synthesis and, more particularly, to the use of these compounds as nucleoside protecting groups. Still more specifically the protecting groups are used in the site-specific stepwise synthesis of oligonucleotides.

2. Description of the Prior Art

Deoxyribonucleic acid ("DNA") and ribonucleic acid ("RNA") are central to information processing in living cells. DNA is the permanent information storage unit, similar to the hard drive on a computer. RNA is the cell's means of transferring and expressing this information from the DNA when necessary, like the RAM in a computer. Both nucleic acid structures are long chain molecules consisting of monomer subunits, the sequence and order of which is the means of coding (FIG. 14), just as the order of letters in a sentence has a specific meaning. There are four monomer building blocks both for DNA and RNA (deoxy-adenosine and riboadenosine are illustrated in FIG. 15). By comparison, the english language uses 26 letters, or building blocks to build a sentence. DNA must be able to store its information permanently and, thus, it is relatively stable. RNA is meant to transfer information temporarily and, thus, is rather easily degraded by enzymes and extreme pH's or other harsh chemical conditions. Although human cells contain ~6 billion base pairs of deoxyribonucleic acid ("DNA"), it is very useful to synthesize and study oligonucleotides, or short lengths of DNA, of 20–30 bases long. Prior to 1982 the synthesis of oligonucleotides was a rather time consuming process which usually required the skills of chemists. The method of building an oligonucleotide chain requires a series of reactions to elongate the chain one monomer at a time. This series of reactions is repeated for each sequential monomer that must be added to this growing oligonucleotide chain.

Conventional phosphoramidite chemistry, so named for a functional group on the monomer building blocks, was first developed in the early 1980's as disclosed in U.S. Pat. No. 4,415,732. This functional group provided a relatively efficient means of joining a building block monomer to the growing chain. Solid phase synthesis disclosed by Caruthers et al. in U.S. Pat. No. 4,458,066 was another improvement to oligonucleotide synthesis. In this technique, the growing DNA chain is attached to an insoluble support via a long organic linker which allows the the growing DNA chain to be solubilized in the solvent in which the support is placed. The solubilized, yet immobilized, DNA chain is thereby allowed to react with reagents in the surrounding solvent and allows for the easy washing away of the reagents from the solid support to which the oligonucleotide is attached. These significant advances in phosphoramidite chemistry and solid phase synthesis paved the way to making custom DNA synthesis accessible to the average biology lab. Techniques like Sanger sequencing, which relies on synthetic DNA, are essential to the Human Genome Sequencing Project. Other novel techniques, e.g. polymerase chain reaction ("PCR"), have been invented due to the ready availability of synthetic DNA. PCR is one of the principal techniques in forensic testing and DNA fingerprinting.

As can be seen in FIG. 15, there are several sites on the nucleosides of similar chemical nature, e.g. —OH or hydroxyl groups. However, as can be seen In FIG. 14, the monomer subunits in DNA and RNA oligonucleotides must be attached in a site-specific manner. This requires functionalizing a site either on the growing chain or on the incoming base for attachment of the incoming monomer building block to the growing chain. To prevent the incoming monomer from attaching at the wrong site, the wrong sites must be blocked while the correct site is left open to react. This requires the use of what are termed protecting groups. Protecting groups are compounds attached temporarily to a potentially reactive site so as to prevent it from reacting. The protecting group must be stable during said reactions and yet must eventually be removed to yield the original site. The synthesis of oligonucleotides requires several sites to be protected and particular sites must be deprotected while others remain protected. These protecting groups grouped together as a set are termed orthogonal protecting groups.

Phosphoramidite chemistry and solid phase oligonucleotide synthesis protocols use a dimethoxytrityl protecting group for the 5' hydroxyl of nucleosides (see FIG. 15 for numbering 1', 2', 3', 4' and 5'). A phosphoramidite functionality is utilized at the 3' hydroxyl position. Phosphoramidite synthesis generally proceeds from the 3' to the 5' of the ribose or deoxyribose sugar component of the phosphoramidite nucleoside (see FIG. 16 for a schematic representation of this technology). The 5' end of the growing chain is coupled with the 3' phosphoramidite of the incoming base to form a phosphite triester intermediate (the 5' hydroxyl of the added base is protected by a dimethoxytrityl group so only one new base is added to the growing chain at a time). Any unreacted 5' hydroxyls are "capped" off to stop the synthesis of this chain, which would be one base short at the end of synthesis. The triester intermediate is subjected to iodine oxidation after each coupling reaction to yield a more stable phosphotriester intermediate. Without oxidation, the unstable phosphite triester linkage would cleave under the acidic conditions of subsequent synthesis steps. Removal or deprotection of the 5' dimethoxytrityl protecting group of the newly added base is typically accomplished by reaction with acidic solution to yield a free 5' hydroxyl group which can be coupled to the next protected nucleoside phosphoramidite. This process is repeated for each monomer added until the desired sequence is synthesized.

The phosphoramidite technique was a significant advance in the art. Nevertheless, several problems are associated with the phosphoramidite protocols. These problems are as follows. All chemicals used in oligonucleotide synthesis must be compatible with the dimethoxytrityl protecting group, and this circumstance precludes the use of incompatible reagents as well as incompatible protecting groups for protecting the 2' position during RNA synthesis. The removal of the dimethoxytrityl group is reversible and, consequently, the cleaved dimethoxytrityl group must be thoroughly removed from the reaction or quenched to obtain maximum yields. Another problem is the various product impurities due to numerous side reactions that accompany the acid deprotection of the 5' hydroxyl during each cycle of base addition. The acidic conditions of deprotection lead to depurination during synthesis and, particularly, depurination of N-protected adenosine.

Attempts to utilize other protecting groups and reagents has largely failed to overcome the depurination problem. Aprotic acid conditions, which do not lead to depurination, work well only for oligonucleotide sequences less than about twelve units in length. The depurination rate is particularly sensitive to the choice of a protecting group for N-6 of adenosine. Phenoxyacetyl amide protecting groups slow the depurination rate relative to the standard benzoyl group by a factor of about two, but depurination remains a problem for long syntheses and large scale reactions. Amidine protecting groups slow depurination by a significant factor of 20, but the commercial wide spread use of amidines in oligonucleotide synthesis has not transpired, despite being described over 10 years ago.

A significant disadvantage of using a 5' dimethoxytrityl group for the synthesis of oligonucleotides is that such use precludes the synthesis of oligonucleotides having acid labile backbones or functionalities. Modified, or unnatural, backbones are often used to impart stability to oligonucleotides which may be exposed to enzymes which degrade oligonucleotides. For example, antisense oligonucleotides which incorporate diamidates, boranophosphates, or acid labile bases may hold promise in pharmaceutical applications, but present dimethoxytrityl synthesis techniques using the dimethoxytryl protecting group precludes the manufacture of these materials by requiring the use of acid deprotection conditions during oligonucleotide synthesis.

The use of the dimethoxytrityl group further prevents the use of other acid labile protecting groups. This is important for RNA synthesis because another hydroxyl group at the 2' position (see FIG. 15) must be protected. The use of the dimethoxytrityl group at the 5' position therefore prevents the successful use of acid labile groups for 2' protection during RNA synthesis.

RNA is more difficult to synthesize relative to DNA. This is not only due to the need for an additional orthogonal protecting group that must be compatible with all other protecting groups but also because of the instability of RNA as mentioned earlier. The significance of this, relative to RNA oligonucleotide synthesis, is that the 2' hyxdroxyl protecting groups preferably should be the last protecting groups removed and must be done so under mild, non-degradative conditions.

RNA is particularly difficult to synthesize with the conventional 5' dimethoxytrityl protecting group due to the difficulty of finding a suitable 2' protecting group. A t-butyldimethylsilyl ether protecting group is presently used at the 2' position in conjunction with the 5' dimethoxytrityl group, but the process lacks reliability. Coupling yields are poor and high pressure liquid chromatography ("HPLC") analysis of RNA product shows significant unexplained impurities. These impurities significantly increase the difficulty of isolating the desired oligonucleotide. Complete deprotection of the t-butyidimethylsilyl group from the oligonucleotide is questionable for long sequences. Deprotection is done in organic solvents which further complicates the isolation of the water soluble RNA from the deprotection reaction. Synthesis of the protected ribonucleosides used for oligonucleotide synthesis is also rather costly and prone to yield impurities that complicate synthesis of natural RNA. As a result of all these complications, the use of a 5' dimethoxytrityl group in conjunction with a 2' t-butyidimethylsilyl protecting group is not reliable or efficient.

Another choice for 2' protection is the acetal class of protecting groups. They can be removed under mild aqueous acidic conditions. This is desirable as a final RNA deprotection step because RNA is soluble in water, is easily isolated from water and is only slightly unstable under conditions for deprotection of some of the more labile acetals. The use of acetals at the 2' hydroxyl position has been attempted in conjunction with a 5' dimethoxytrityl group, but very stable acetals must be used with the acid labile dimethoxytrityl group. Removal of acetals that are stable under dimethoxytrityl deprotection conditions requires strong acidic conditions that degrade the RNA. Acetals have been attempted with alternative 5' protecting groups which are deprotected under non-acidic conditions, e.g. leuvinyl, but without significant success.

Oligonucleotide synthesis according to H-phosphonate protocols will permit a single oxidation step at the conclusion of the synthesis cycles. However, coupling yields are less efficient than those for phosphoramidite chemistry and oxidation requires longer times and harsher reagents than amidite chemistry.

There remains a need to find an alternative 5' protecting group that permits the use of acid labile linkages, reagents and protecting groups that are incompatible with dimethoxytrityl, increased process yields, and reduction of product impurities without significant increase in cycle times. An alternative 5' protecting group would further be a significant advantage for RNA synthesis by allowing the use of more suitable 2' protecting groups.

SUMMARY OF THE INVENTION

Accordingly, it is an object of this invention to provide useful protecting groups and methods for the improved synthesis of RNA.

It is further an object of this invention to provide useful protecting groups for the improved synthesis of DNA.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

The present invention achieves the foregoing and other objects via novel protecting groups. This invention also describes methods to apply these novell protecting groups to RNA and DNA synthesis. Additionally, these protecting groups may more generally be used in any site specific, step-wise synthesis of polymers in addition to nucleotide polymers. Still more generally, these protecting groups may be used in any organic synthesis.

The present invention in its broadest sense encompasses materials and methods for use in site-specific step-wise synthesis that yield polymer chains, e.g., as in the formation of oligonucleotides and oligosaccharides. The synthesis protocol begins with the preparation of a first chain including at least one substituted monomer. This preparation step preferably includes attaching the substituted monomer to an insoluble polystyrene support. The substituted monomer is deprotected if necessary to expose a reactive site. A second protected monomer is provided having a silyl protecting group and/or an orthoester protecting group at specific sites. The second protected monomer is reacted with the deprotected site of the chain to yield an elongated monomer chain.

The protecting group at the elongation point of this chain is deprotected to expose a reactive site ready to connect with the third substituted monomer with silyl and/or orthoester protecting groups. The synthesis method disclosed above is repeated until the desired chain length is achieved.

A particularly preferred embodiment includes use of a 5' silyl protecting group and a 2' orthoester protecting group in the solid support synthesis of ribo-oligonucleotides via phosphoramidite chemistry. In this embodiment, the first nucleotide chain includes a first monomer unit. Addition of each subsequent monomer in the chain requires a cycle of reactions. During each cycle, the second protected phosphoramidite monomer is coupled to the exposed reactive site of the first chain to yield a phosphite triester linkage via the 5' end of the chain and the 3' end of the added monomer. The cycle of steps to provide and attach the second protected monomer to the chain, deprotect the second monomer now attached to the chain, and couple the third monomer to the deprotected site on the chain are repeated for each additional monomer added to the chain. The synthesis can be used to construct specific sequences of DNA and RNA or functional homologues thereof.

The term "functional homologues" is hereby defined to mean polymers that deviate in some manner from naturally occurring substances according to textbook definitions, and are understood by those skilled in the art to function in a related manner. These non-natural oligonucleotides may include radiolabeled nucleotides, nucleotides having chromophores attached, sugars other than ribose or deoxyribose, oligomers having alternative phosphate linkages, e.g. methyl phosphonates, thiophosphates, boranophosphates, fluoridated ribose (or other halogens), alkyl ethers, substituted sugars, other substituted sugars and base-like materials having carbon and non-carbon heterocyclic moieties, e.g. 5-bromo-uridine. Additionally, the conventional bases are understood to include adenine, guanine, cytosine, thymine, and uracil.

A preferred method step of oligonucleotide synthesis includes the addition of fluoride ion to remove the silyl protecting group. This alternative for the repetative 5' deprotection conditions has resulted in higher process yields and fewer side products. As a result, purification of the full length product is greatly simplified by the substantial absence of side-products which are very close to the full length product. Coupling of a protected phosphoramidite monomer with the deprotected end of the growing oligonucleotide chain is facilitated by the use of a suitable catalyst, e.g., tetrazole, which yields a phosphite triester bridge that is stable under fluoride deprotection conditions. In contrast, conventional phosphoramidite oligonucleotide synthesis reactions require acid deprotection conditions that degrade the phosphite triester linkage. This circumstance of the conventional process requires an additional oxidation step in each cycle to convert an unstable phosphite triester into a more stable phosphotriester. In the present case, the oxidation step is avoided by the absence of the acid-labile dimethoxrityl protecting group, and full chain oxidation of the oligonucleotide sequence is conducted in one step at the conclusion of the synthesis.

The 5' silyl group includes a central silicon atom with four substituents attached. These substituents may be independent of one another or connected, e.g. to form a ring. One of these substituents is the protected 5' nucleoside hydroxyl. At least one of the three other substituents must be a siloxy or an alkoxy group. Preferably, all three other substituents are siloxy or alkoxy groups (any combination of siloxy and alkoxy groups is allowed).

RNA synthesis requires a second protecting group located at the 2' position of the ribose ring in addition to a 5' protecting group. These orthogonal protecting groups are such that the 5' protecting group is removed by fluoride ions or other non-acidic reagents and the 2' protecting group is removed under acidic conditions. More specifically, the present invention for RNA synthesis utilizes an orthoester protecting group at the 2' position and a silyl group at the 5' position. The silyl group is as described in previous paragraph. The orthoester protecting group is preferably a non-cyclic orthoester. The orthoester reagent consists of three ether groups one of which attaches to the 2' hydroxyl group of the nucleoside to be protected. The other two substituents of the orthoester reagent can be any organic group. Preferably these two substituents are identical. Additionally, these substituents have some electron withdrawing capabilities. The use of an orthoester as a 2' protecting group permits the final ribo-oligonucleotide deprotection conditions to be mild and essentially non-degradative to the RNA product.

BRIEF DESCRIPTION OF THE DRAWINGS

The accompanying drawings, which are incorporated in and form a part of the specifications, illustrate the preferred embodiments of the present invention, and together with the description serve to explain the principles of the invention.

FIG. 1 depicts a nucleoside having a silylether protecting group bonded to the 5' carbon, as well as multiple substituents that may be combined to form the silylether protecting group according to the present invention;

FIG. 1(A) presents fluoride lability results that were obtained from various compounds that were made from the various substituents of FIG.1;

DETAILED DESCRIPTION OF THE PREFERRED EMBODIMENT

Figure 2:
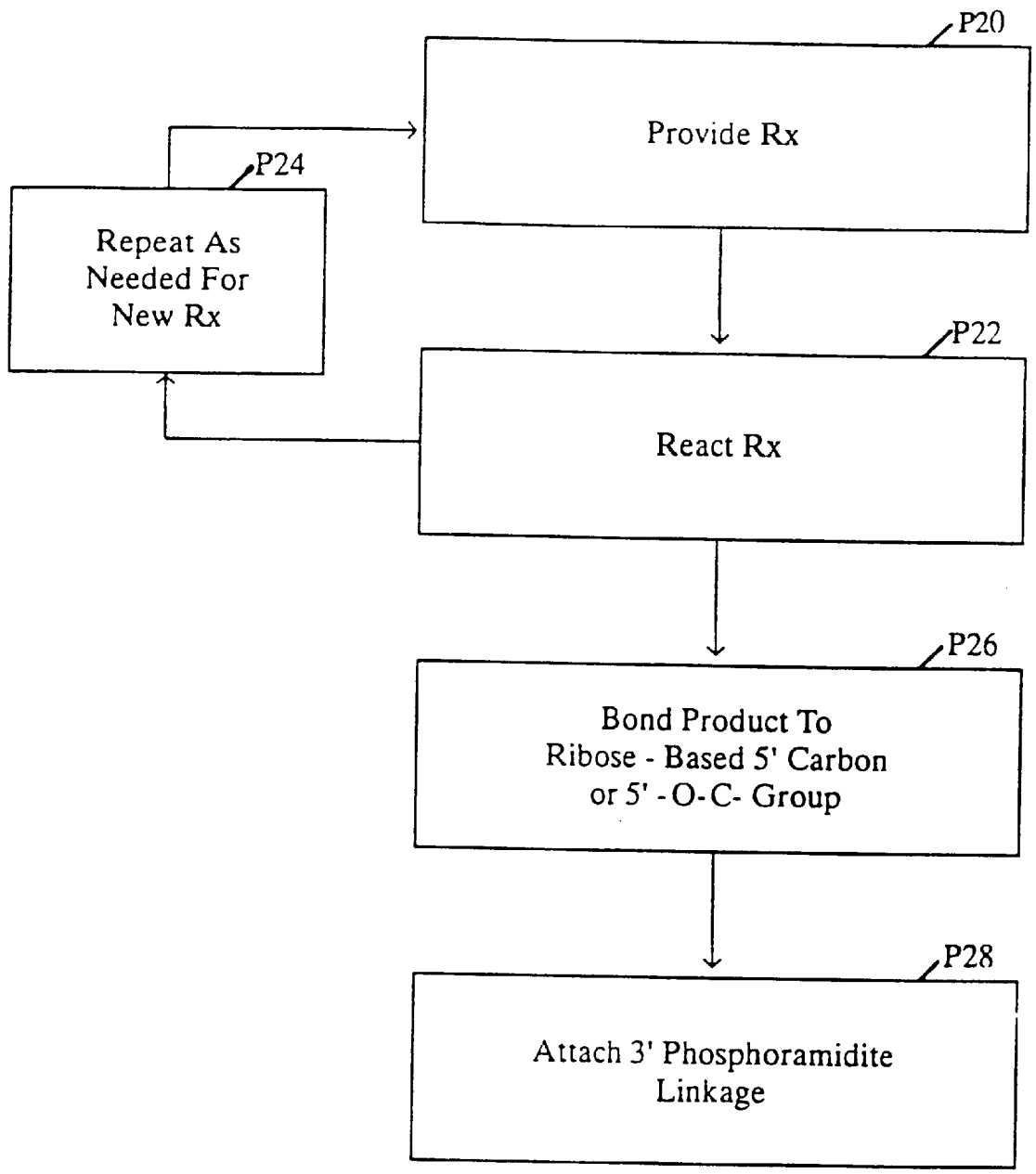
FIG. 2 depicts a flow diagram that describes the synthesis of the precursor shown in FIG. 1 followed by phosphoramidite conversion of the precursor shown in FIG. 1.

5'-O-silylether protected nucleosides are synthesized that are suitable for solid support synthesis of oligonucleotides. This 5' silyl protecting group is used in conjunction with acid labile orthoesters at the 2' position of ribonucleosides to synthesize ribo-oligonucleotides via phosphoramidite chemistry. Bis-(2-butyne) orthoesters are used for uridine and N-benzoylcytidine. Bis-phenoxyethyl orthoesters are used for benzoyl-adenosine and N-isobutyryl-guanosine. These protecting groups and the associated synthesis methods require less time than current methods to synthesize ribo-oligonucleotides. Final deprotection conditions in this synthesis are aqueous buffers of low pH for a sufficient period of time at 5–95° C. These conditions do not significantly degrade the RNA product. The final product is produced in better yields and with better quality, i.e. with fewer side products, compared to current 5'-O-dimethoxytrityl nucleoside based RNA synthesis methodologies. When used for synthesis of DNA oligonucleotides the 5'-silyl protecting group enables the successful synthesis of oligonucleotides without depurination side products associated with conventional 5'-O-dimethoxytrityl nucleoside based syntheses. All syntheses are accomplished without oxidation of phosphite triester intermediates until one final oxidation step.

A 5'-OH nucleoside protecting group preferably performs numerous functions in oligonucleotide synthesis. The group selectively reacts with the 5'-OH, thereby allowing a high yielding synthesis of protected nucleoside monomers. The group is preferably stable under amidite synthesis conditions, storage conditions, and oligonucleotide synthesis conditions. Rapid removal, i.e., less than one minute, of the group from a support-bound oligonucleotide is very desirable to speed up synthesis times and reduce prolonged exposure of the growing oligonucleotide to reagents. Oligonucleotide synthesis is improved if the 5' protecting group is visible during deprotection, e.g., from the addition of a chromophore silyl substituent. Additionally, the cost must not be prohibitive. The essential characteristics include stability under all synthesis and storage conditions, as well as rapid removal.

Selection of protecting groups is complicated by the competing demands of the essential characteristics of stability and easy removal, and the need to balance these competitive goals. Most substituents that increase stability also Increase the time it takes to remove the overall group, but the increase in stability and/or 5' selectivity correspondingly increases the level of difficulty in removal of the group.

The addition of alkoxy and siloxy substituents to the 5' silylether protecting group increases the susceptibility of the protecting groups to fluoride cleavage of the silylether bonds. Increasing the steric bulk of the substituents preserves stability while not decreasing fluoride lability to an equal extent. An appropriate balance of substituents on the silyl group makes a silyl ether a viable 5'-OH nucleoside protecting group.

In the context of phosphoramidite oligonucleotide synthesis, however, simply replacing a 5'-O-dimethoxytrityl group with a 5'-O-silyl group and changing the deprotection conditions fails to provide a viable oligonucleotide synthesis. Several unobvious and novel modifications to the process are required. The 5'-O-silyl group is most effectively removed via fluoride ions. Fluoride ion sources can include any source of fluoride ion, e.g., from inorganic fluoride salts such as cesium fluoride and potassium fluoride to organic salts such as tetrabutylammonium fluoride. A crown ether catalyst is preferably utilized in combination with the inorganic fluoride salts to optimize their effect. Tetrabutylammonium fluoride is usually the preferred fluoride source. However, tetrabutylammonium fluoride deprotection of a 5'-O-silyl group during oligonucleotide synthesis, gave inconsistent results with comparatively lower full length yields and products contaminated with impurities. It was discovered that the most preferred fluoride ion sources for this invention were aminehydrofluorides. The choice of protecting groups for use on the phosphite triesters and phosphotriesters affects the stability of the triesters towards fluorine. Methyl protection of the phosphotriester or phosphitetriester was found to stabilize the linkage against fluoride ions and improve process yields. Also, methyl protection allows for synthesis of oligonucleotide sequences without oxidizing each cycle. Oxidation of the phosphite triester product in phosphoramidite chemistry is quicker and produces fewer undesired side-products than does the one-step oxidation of H-phosphonate chemistry. Therefore, the use of fluoride-labile protecting groups with phosphite triester linkages permits the use of milder oxidation conditions and higher process yields than with H-phosphonate chemistry.

Still further modifications needed to be made. Standard control pore glass solid phase synthesis supports can not be used in conjunction with fluoride labile 5' silyl protecting groups because the glass is degraded by fluoride with a significant reduction in the amount of full-length product. Fluoride-stable polystyrene based supports are preferred.

Ribonucleosides have a reactive 2' hydroxyl substituent. In contrast, deoxynucleosides have no reactive 2' reactive substituent Accordingly, it is desirable to protect the reactive 2' position in RNA with a protecting group that is compatible with a 5'-O-silyl protecting group, e.g. one stable to fluoride. Orthoesters were developed for stability under all synthesis conditions and workup reactions, yet these orthoesters were readily removed in a final acid deprotection step that minimized RNA degradation.

Further modifications needed to be made for RNA synthesis. The standard phosphoramidite coupling catalyst tetrazole was found to be inadequate for this invention, as determined by relatively lower process yields. Stronger reagents, e.g. S-ethyl-tetrazole, p-nitrophenyltetrazole, are preferably utilized to increase the process yield.

FIG. 1. presents nucleoside monomer Formula (I) and various substituents that may be appended to Formula (I). In Formula (I), R' is preferably a 2' orthoester protecting group in the case of RNA synthesis (protecting the 2' ribose hydroxy moiety), H in the case of DNA synthesis, or any other compatible moiety, e.g., ethers, alkyl ethers, esters, halogens, protected amines, and protected hydroxyl moieties; R" can include any moiety as a precursor to the final monomer, however, R" is preferably a phosphoramidite linkage and, more preferably, R" is a phosphoramidite linkage as shown in Formula (1A) wherein $R_4$ may be any compatible organic ligand; $R_1$, $R_2$, and $R_3$ include at least one alkoxy or siloxy substituent, and may be any one of substituents (A), (B), (C), (D), (E), (F), (G), (H), (I), and (K), or compounds of similar molecular weight and steric bulk; BASE is a nucleic acid base which may include adenine, guanine, cytosine, thymine, uracil, N protected adenine, guanine and cytosine or functional homologues thereof. The respective portions of Formula (I) include a central ribose-based sugar having a nucleic base connected to the 1' ribose position, a hydroxy moiety connected to the 3' ribose position, and a silylether connected to the 5' ribose position. The broken line attached to each of the substituents (A) through (K) indicates a locus for attachment to the 5' silicon moiety.

As indicated above, Formula (I) represents a precursor to the phosphoramidite nucleoside for use in oligonucleotide synthesis when R' is not a phosphoramidite moiety. A phosphoramidite moiety is preferably attached to the precursor when R" is a hydroxy moiety. Subsequent to the synthesis of 5'-O-silyl protecting group including $R_1$, $R_2$, and $R_3$, the 3' OH group is preferably converted to a phosphoramidite linkage by conventional protocols using bisdiisopropylaminemethoxyphosphine, as will be understood by those skilled in the art. The present synthesis technique is also fully compatible with other types of phosphoramidite linkages, such as those described in U.S. Pat. No. 4,415,732 which is hereby incorporated by reference herein to the same extent as though fully disclosed herein. Formula (I) including any combination of $R_1$, $R_2$, and $R_3$ substituents A–K can be synthesized from commercially available precursors, or synthesized as described below or as described in the literature.

FIG. 2 depicts an exemplary flow diagram that describes the synthesis of the Formula I precursor (when R" is —OH) followed by phosphoramidite conversion of the Formula I precursor. Step P20 includes providing an $R_X$ compound corresponding to a silyl group with one or more of the desired substituents, $R_1$, $R_2$, and $R_3$. This compound is preferably provided via commercial sources, e.g., where $R_1$ is an alkyl group as with substituents A and D (see FIG. 1), or by reacting $SiCl_4$ with an alcohol as with substituents B and K, or by reacting $SiCl_4$ with sodium salt of silanol or alcohol as with substituent E.

Step P22 includes reacting the $R_X$ compound with an appropriate alcohol or silanol. The product may be purified or used as is or with minor purification.

Step P24 includes repeating steps P20 and P22 up to one more time for triple substitution of the intermediate reaction product. Each repeat cycle of Step P20 may provide a new $R_X$ corresponding to one of substituents A–K of FIG. 1, or $R_X$ may remain the same. It is preferred to include at least one alkoxy or siloxy substituent selected from substituents C, because these substituents enhance fluoride lability of the 5' silylether.

Step P26 includes substituting the silyl group derived from Step P24 for the hydrogen connected to the 5' oxygen of the nucleoside of Formula (I). The substitution reaction is preferably facilitated by the addition of an imidazole catalyst, and is site-specific for the 5' hydroxyl. A nucleoside moiety including a specific BASE is preferably combined with the silyl group in the presence of the imidazole catalyst and reacted at room temperature for one hour or more.

Step P28 includes attaching a phosphoramidite functional group to the 3' hydroxyl of the silyl protected product derived from Step P26. A suitable solvent, e.g., anhydrous dichloromethane, is combined with the silyl group product and an excess amount of bis-diiosopropylmethoxyphosphine in the presence of a catalytic amount of tertrazole. The phosphorylation reaction conducts a site specific phosphoramidite substitution of the hydrogen connected to the 3' oxygen of Formula (I).

EXAMPLE 1

Synthesis of 5' O-Silyl Protected 3'O-Diisopropylmethoxyphosphine-Thymidine

Figure 3:
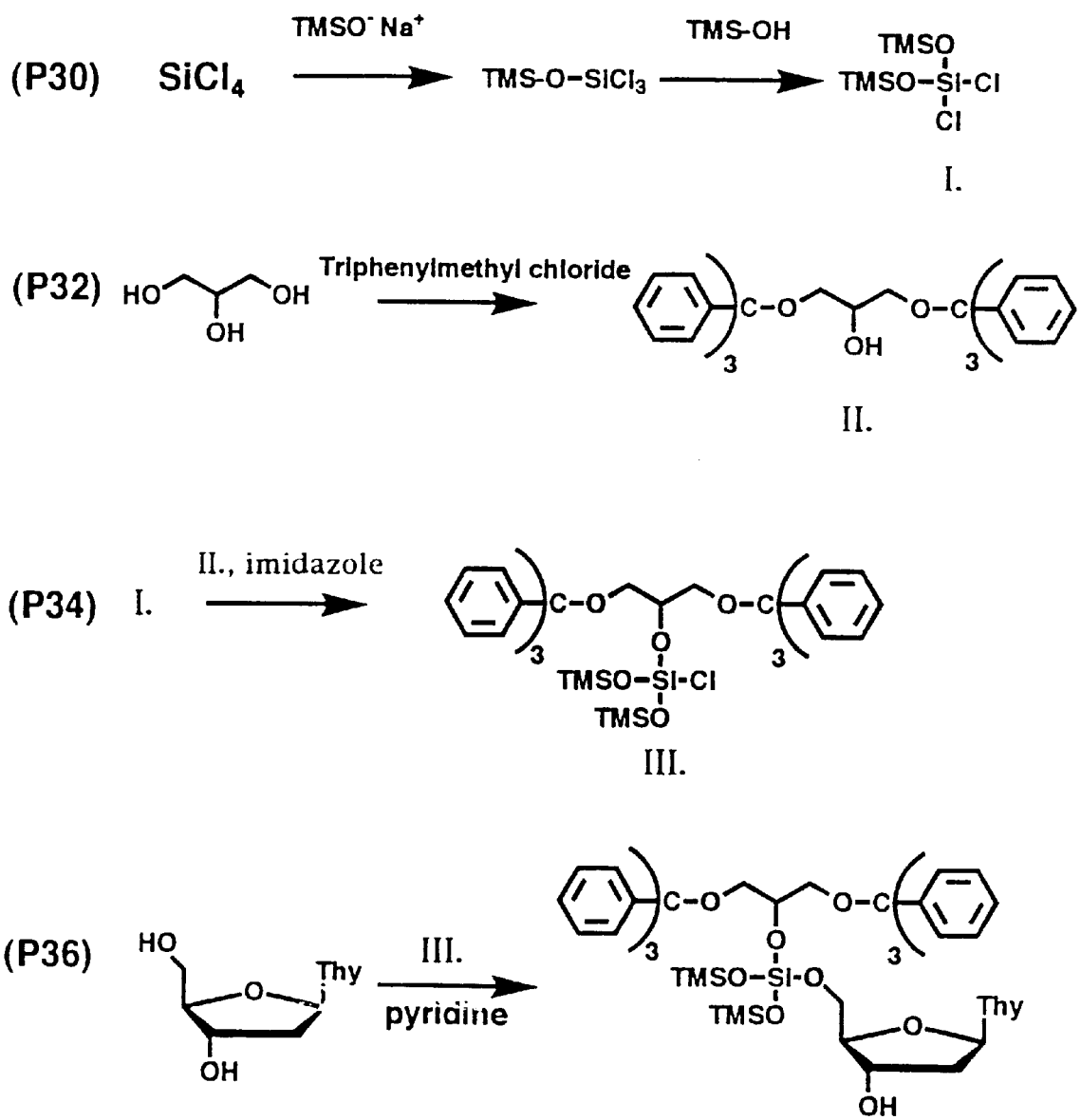
FIG. 3 depicts a detailed reaction process that embodies a portion of the process shown FIG. 2.

FIG. 3 depicts a detailed reaction process including Steps P30–P36, which also embody Steps P20 through P26 of FIG. 2. In this process, bis-trimethylsiloxy-dichlorosilane and bis-tritylglycerol were synthesized separately, combined, and then used to protect the 5'-OH of a 2'-deoxythymidine nucleoside. The reagents utilized in this example can be obtained from a variety of commercial sources, e.g., Aldrich Chemical of Milwaukee, Wis.

Step P30 included synthesis of bis-trimethoxy-dichlorosilane.

Trimethylsilanol ("TMSO$^-$OH") was formed by adding 10.4 moles of hexamethylsilazane (84 ml) to a stirred solution including 0.4 moles of glacial acetic acid (22.8 ml) in 400 ml of distilled water at 0° C. The aqueous phase was removed and washed twice with 100 ml of ether. The ether washes were combined with the silanol phase and stored at −20° C. to freeze out the excess water. The liquid solution was decanted and dried over potassium carbonate for 75 min, diluted to 750 ml with ether, passed through a 0.45 $\mu$m filter and used in the next synthesis. Nuclear magnetic resonance analysis indicated the formation of disiloxane in an amount ranging from about three to four mole percent relative to product.

Sodium trimethylsilanate ("TMSO$^-$Na$^+$") was prepared by reacting the trimethylsilanol in ether solution with 0.88 moles (21.1 g) of sodium hydride suspended in 500 ml of anhydrous tetrahydrofuran solvent under vigorous stirring conditions at 0° C. Stirring was continued for one hour at room temperature after the trimethysilanol solution was added by cannula. The reacted solution was filtered through celite for later use. Disiloxane concentration in the solution was determined to be 17% by nuclear magnetic resonance analysis.

Trichloro-trimethylsiloxy-silane was prepared by reacting an aliquot of the sodium trimethylsilanate solution containing 0.663 moles of sodium trimethylsilanate with 0.597 moles (68.5 ml) of tetrachlorosilane. The trimethylsilanate solution was added by cannula to a mechanically stirred solution of the tetrachlorosilane 500 ml of ether at 0° C. The salt was removed by centrifugation (8000 rpm for 10–15 min). and the solution was decanted off. The ether was removed in vacuo and the product was distilled at atmospheric pressure. Distillation commenced at an oil temperature of 122° C. and continued to an oil temperature of 185° C. to collect dichloro-bis-trimethylsiloxy-silane. The product contained 87.91 mole percent trichlorotrimethylsiloxy silane, 5.86% dichloro-bis-trimethylsiloxysilane, and 6.22% disiloxane. The crude product was not subjected to further purification.

Bis-trimethylsiloxy-dichlorosilane was synthesized by reacting 0.3681 moles of trichlorotrimethylsilane in the crude reaction product with a 1.1 molar equivalent of trimethylsilanol prepared as before. The trimethylsilanol was cannulated to a mechanically stirred solution including the crude trichlorotrimethylsilane reaction product and 1.47 moles (205 ml) of triethylamine in 1000 g of ether at 0° C. The solution was filtered under argon and the solvent was removed in vacuo. The product was fractionally distilled over calcium hydride at 60° C. and a pressure of 4 mm Hg to yield the bis-trimethylsiloxy-dichlorosilane reaction product and complete Step P30.

Step P32 included synthesis of 1,3-O-bistritylletherglygerol.

The 1,3-O-bistrityletherglygerol was prepared by adding 0.304 moles (28 g) of dry glycerol to 0.608 moles (169.52 g) of triphenylmethylchloride in 400 ml of pyridine solvent at 0° C. The reaction continued to completion overnight at room temperature. The product was purified on silica gel after an aqueous workup, and then crystallized to complete Step P32.

Step P34 included combining the products from Steps P30 and P32.

A 12 mmole (6.919 g) aliquot of the 1,3-O-bistritylethergylcerol reaction product and mixed with 40 mmole (2.723 g) of imidazole were mixed with pyridine solvent and coevaporated. A 40 ml amount of pyridine was added and the solution was cooled to 0° C. in an ice bath. The resultant solution was rapidly stirred while 10 mmole (2.772 g) of bis(trimethylsiloxy) dichlorosilane was added dropwise over a 1 minute time period. The solution was removed from the ice bath and stirred at room temperature for 15 minutes to complete step P34.

Step P36 included addition of the product from step P34 to a thymidine nucleoside.

A 12 mmole (2.904 g) quantity of 2'-deoxythymidine was coevaporated with pyridine and then resuspended in 24 ml pyridine. The silyl solution from Step P34 was added dropwise over 30 min to the rapidly stirred thymidine solution at 0° C. The reaction was continued at room temperature for 1 hr. Thin layer chromatography utilizing a solvent including a 40:60 mixture of hexanes:ethyl acetate indicated that the reaction was complete. Distilled water (1 ml) was added and the solvent was removed in vacuo. An aqueous workup followed by column purification on 600 ml silica with an elution solvent comprising a 50:50 mixture of hexanes:ethyl acetate) yielded 4.88 g of a product having a 1023.05 g/mole molecular weight, i.e., 4.77 mmole for a 47% yield. The product was crystallized from a mixture of ethyl acetate and pentane to remove a trace 3'-O-silyl nucleoside contaminant to complete Step P36.

The product derived from Step P36 was reacted to form a 5'-O-silyl protected 3'-O-diisopropylmethoxyphosphine-thymidine. A 1.783 mmole (1.824 g) aliquot of the 5'-O-silyl thymidine reaction product from Step P36 was dissolved with 654 µl of bis-diisopropylmethoxyphosphine in 20 ml of anhydrous dichloromethane to form a reaction mixture. A 0.5M quantity of tetrazole was mixed with 1.7 ml of acetonitrile and added to the reaction mixture with stirring for 8 hours at room temperature. Thin layer chromatography utilizing a 65:35:1 solvent mixture of hexanes:ethyl acetate:triethylamine indicated that the reaction was complete. An aqueous workup followed by silica gel purification provided a 67% product yield of the 5' silyl protected phosphorylated nucleoside.

FIG. 1(A) presents fluoride lability results that were obtained from various compounds that were made according to Example 1 from the various substituents of FIG. 1. FIG. 1(A) is provided immediately beneath FIG. 1 for easy reference thereto. For example, the first formulation listed in FIG. 1(A) derived from a combination of substituents A, A, and B as $R_1$, $R_2$, and $R_3$. FIG. 1 and FIG. 1(A) include substituents that have actually been found to work in the laboratory, but are not meant to be comprehensive lists of all substituents that will work. Additionally, any compatible alkoxy or siloxy substituent may be used having a molecular weight and/or steric bulk that approximates the substituents of FIG. 1 and FIG. 1(A). The number of useful substituents is very large, and will permit the incorporation of a chromophore, e.g., a dansyl moiety, into a silyl group corresponding to one of the $R_x$ positions of Formula I. The second column includes a comparison of the time to a complete reaction that removed the fluoride labile silyl group. The time to a complete reaction was determined by thin layer chromatography from a solution including the respective Formula (I) precursors in a tetrahydrofuran solvent mixed with a molar fraction of the precursor and five equimolar fractions of tetrabutylammonium fluoride. The precursors having lower reaction times are more preferred, with the I-I',E,E precursor being most preferred.

Figure 4:
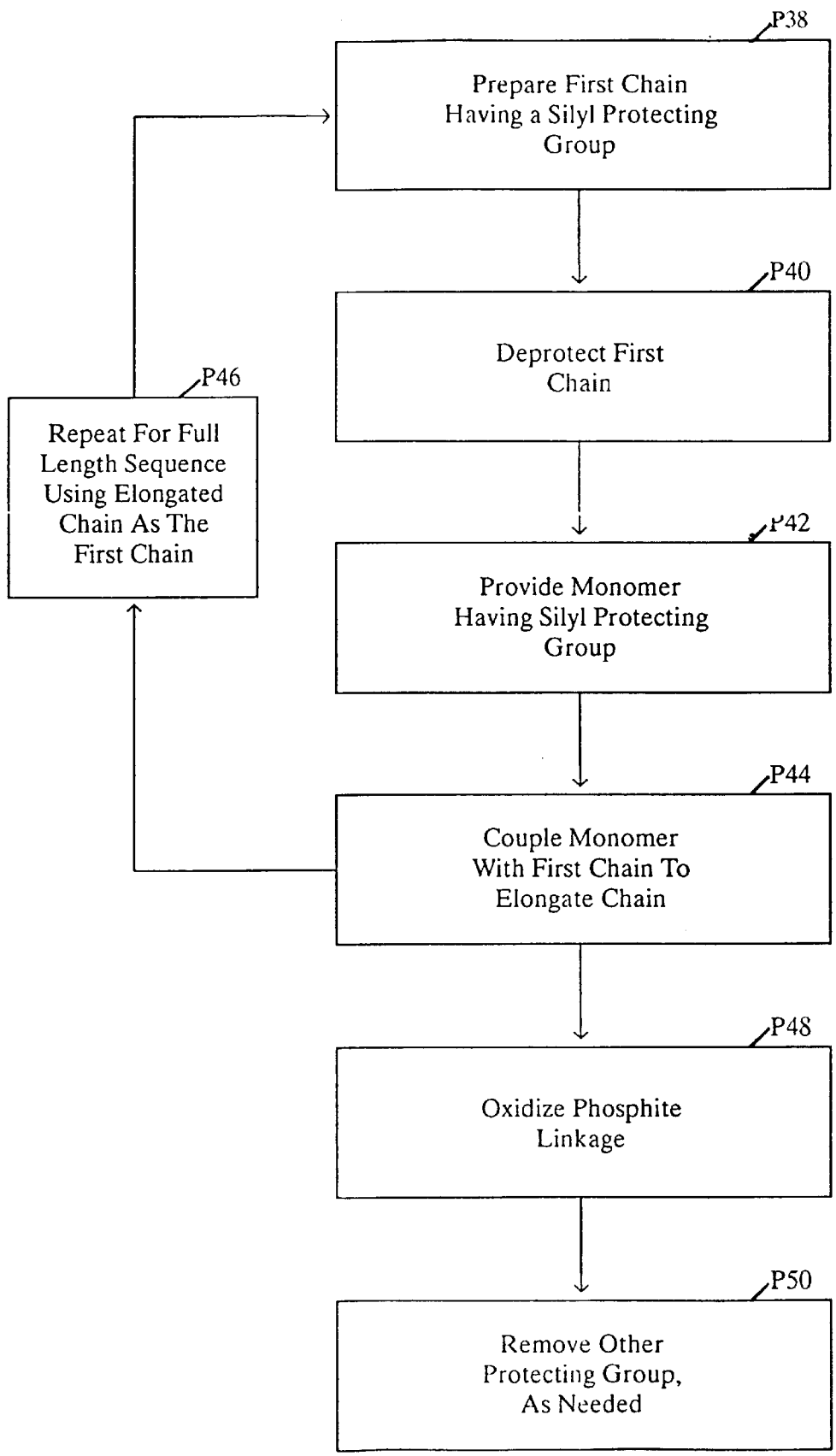
FIG. 4 depicts a generalized flow diagram for using silyl protecting groups to synthesize polymers.

FIG. 4 depicts a generalized schematic block process diagram for using silyl protecting groups to synthesize polymers. This process generally lends itself to any polymer synthesis, but preferred embodiments include the synthesis of sugar chains, such as oligosaccharides, oligonucleotides, and the like.

Step P38 includes preparation of a first chain including at least one monomer having a silyl protecting group. This chain is preferably a nucleotide chain or functional homologue thereof. The preparation step preferably includes attaching the first chain to an insoluble support, such as a polystyrene support. The use of a polystyrene-based support is most preferred due to the tendency of fluoride ion to attack and degrade glass. The reaction can also occur in solution without a solid phase support, but this mode of reaction enhances the difficulty in purification of the final product. In oligonucleotide synthesis, the support is preferably bound to the 3' end of the first nucleotide. The silylether bond will, accordingly, be located at the 5' ribose position for a 3' to 5' direction specific synthesis. Those skilled in the art will understand that a reverse direction (5' to 3') synthesis is possible, but the reverse direction synthesis is less preferred because of increased costs associated with commercially available reagents.

Step P40 includes deprotecting the first chain by removing the silyl protecting group. This step preferably involves fluoride assisted cleavage of the silylether (Si—O) bond.

Step P42 includes providing a monomer having a silyl protecting group. In oligonucleotide synthesis, the monomer is preferably a phosphoramidite nucleoside having a 5' silyl protecting group. In RNA synthesis, the nucleoside preferably has a second protecting group comprising an orthoester at the 2' ribose position. These monomers, as well as monomers used to prepare the first chain of Step P38, can be synthesized according to the generalized process of FIG. 2.

Step P44 includes coupling or reacting the monomer of Step P42 with the deprotected chain of Step P40. The coupling reaction generally follows established conventional protocols for phosphoramidite coupling reactions, with the exception that substituted tetrazole catalysts can provide enhanced yields in some RNA syntheses, and may be advantageously utilized as a replacement for the conventional tetrazole catalyst. The coupling reaction will not be complete in each cycle as some deprotected chains will fail to react with the phosphoramidite nucleoside of Step P42. Therefore, the coupling step is preferably completed by capping the unreacted chains to prevent the production of quasi-full length chains that lack a few nucleotides of the true full length sequence. The shortened chains are later easily removed in column purification. Capping is preferably conducted by the addition of commercially available standard mixtures including acetic anhydride ("$Ac_2O$") and N-methyl imidazole or dimethylaminopyridine ("DMAP").

Step P46 includes repeating Steps P38, P40, P42, and P44 until the number of cycles is sufficient to provide a full length chain including the desired nucleotide sequence. In oligonucleotide synthesis, Step P42 can vary for each respective cycle by providing a nucleoside having a base corresponding to the desired sequence.

Step P48 includes oxidation of the phosphite triester chain linkage to form a phosphotriester linkage. Oxidation is preferably conducted by the addition of t-butylperoxide in toluene. It will be understood, however, that oxidation is not completely conventional because Step P48 is conducted after the full length sequence is constructed. It is often desirable to conduct Step P48 prior to step P50 because the deprotection conditions that may exist in Step P50 will degrade the phosphite triester linkage.

Step P50 includes removal of remaining protecting groups. In the case of RNA synthesis, Step P50 preferably includes a final acid deprotection for removal of the preferred orthoesters.

EXAMPLE 2

Oligonucleotide Synthesis Protocols

Oligonucleotide synthesis was conducted on a Gene Assemble Plus synthesizer from Pharmacia of Milwaukee, Wis. The protocols can be adapted by those skilled in the art to any commercially available synthesizer. A solid support was used for all syntheses, and included a thymidine polystyrene support with succinate linker from Pharmacia packed in 0.2 or 1.0 μmole columns purchased form Miligen of Milford, Mass. The silyl deprotection reagent is as follows: 0.5M aqueous HF solution purchased from Mallinkrodt and 3.5M triethylamine ("TEA") solution in N-methylpyrrolidone ("NMP"). Wash solvents were acetonitrile ("MeCN") and a 1:1 mixture of TEA:NMP. Amidites were dissolved to 0.1M in acetonitrile. The coupling catalyst was 0.45M tetrazole for DNA synthesis and 0.15M S-ethyl-tetrazole for RNA synthesis. The coupling time for DNA synthesis was one minute and in four minutes for RNA synthesis. Capping solutions included commercially available standards of acetic anhydride and N-methyl imidazole or dimethylaminopyridine. Final oxidation of the full length sequence was conducted using 3M t-butylperoxide in toluene. Table 1 includes an outline of the oligonucleotide synthesis cycle conditions following the generalized process depicted in FIGS. 4 and 5.

TABLE 1

OLIGONUCLEOTIDE SYNTHESIS OUTLINE
DNA SYNTHESIS CYCLE USING 5'-O-SILYL GROUP*

| Process Step:Activity | Reagent | Time (Seconds) |
|---|---|---|
| P52: 5' silyl deprotection | 0.5 M HF & 3.5M TEA in NMP | 20 |
| Wash | 1:1 TEA/NMP | 24 |
| Wash | MeCN | 100 |
| P58: Couple | 15 eq. Amidite/100 eq. tertrazole | 60 |
| Wash | MeCn | 30 |
| P62: Capping | acetic anhydride and DMAP | 30 |
| Wash | MeCN | 20 |
| Wash | 1:1 TEA/NMP | 24 |

*Synthesis was followed on the machine by a 45 second oxidation with t-butylperoxide in toluene.

The support column is removed from the synthesizer at the conclusion of the chain-elongation cycles that are conducted according to Table 1. A deprotection mixture is prepared to contain 200 mg of disodium-2-cobamoyl-2-cyanoethylene-1,1-ditiolate trihydrate ("dithio sodium salt") in 800 ml of dimethyl formamide ("DMF"). The deprotection mixture is syringed through the column for fifteen minutes to remove methyl protecting groups on phophotriesters. The column is next washed with distilled water then acetone, and air dried. The support is removed and placed in a sealed vial containing a mixture of 750 μl $NH_4OH$ and 250 μl ethanol for a sixty minute incubation at 65° C. (16 hr for N-benzoyl-adenosine and hisobutyrl-guanosine) to remove base protecting groups and cleave oligonucleotide from the support. The liquid is removed from the vial, dried down, resuspended in water, quantified and analyzed by reverse phase or ion exchange high pressure liquid chromatography ("HPLC").

RNA synthesis requires some slight differences with respect to the DNA synthesis protocols of Table 1. Orthoesters are used as 2'-OH protecting groups for RNA synthesis, and Step P58 utilizes 0.15M S-ethyl-tetrazole in place of the tetrazole catalyst in Table 1. Following $NH_4OH$ deprotection, the product is dried down and redissolved in 0.05M potassium phosphate buffer (pH 3.0) and incubated at 65° C. for 1 hr. Acid deprotection of homopolymers of rA and rC have failed at room temperature but do work for homopolymers of U. This failure is presumed to occur due to secondary structure, but heating of the samples will result in successful deprotection. Applicants theorize that the addition of high salt (e.g. NaCl) to the solution will disrupt secondary structure of hydrophilic orthoesters and result in a room-temperature deprotection. Acid deprotection is preferably followed by the addition of 0.15M tris (pH 8.5) for 30 min at 65° C. to remove 2'-O-formyl groups, which are byproducts of acid deprotection. 2'-O-formyl groups are easily removed above pH 7. RNA products are preferably analyzed by HPLC with no further workup.

Figure 5:
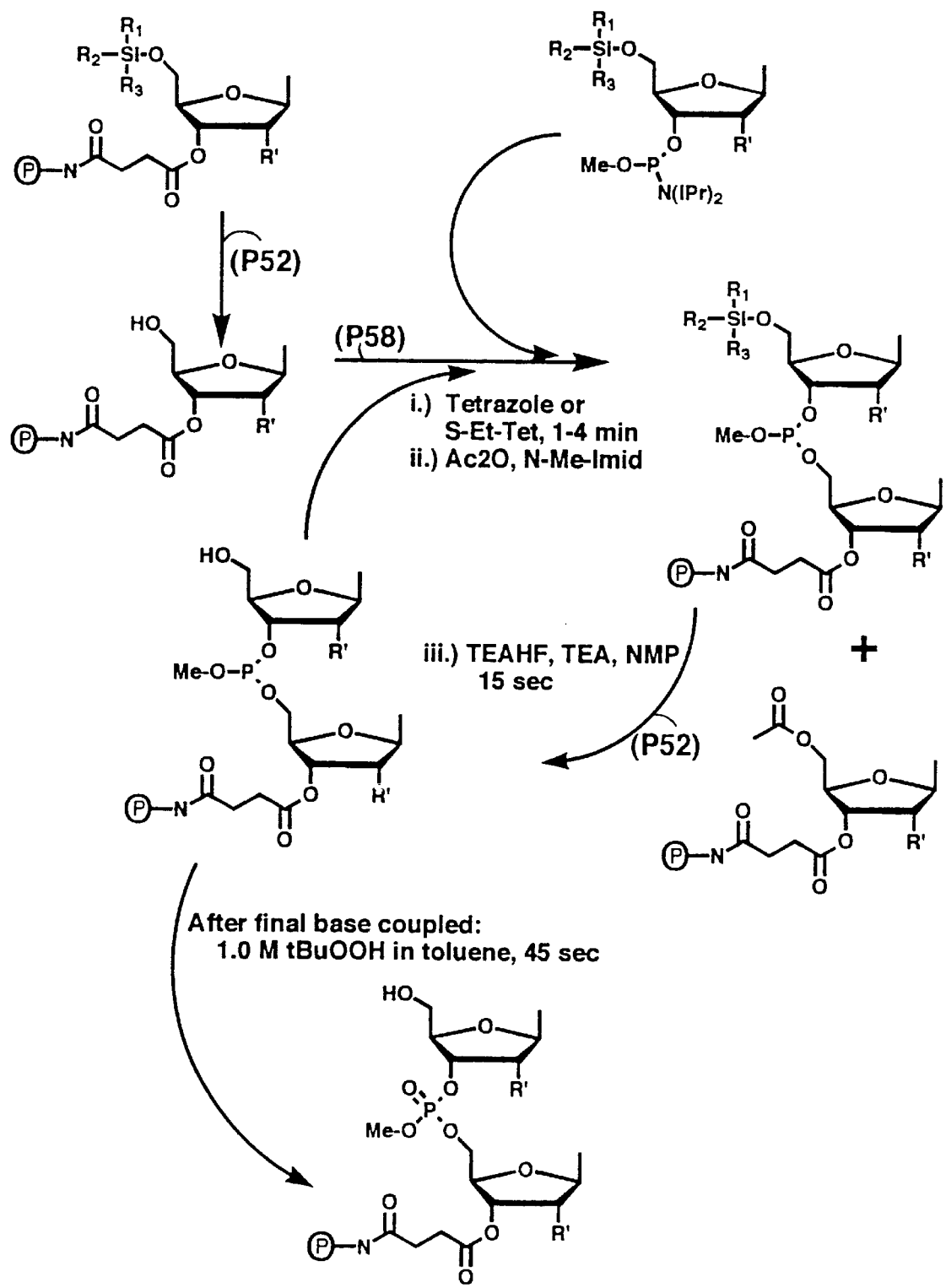
FIG. 5 depicts the chemical reactions involved in synthesizing an oligonucleotide according to the present invention.

FIG. 5 depicts the reactions involved in synthesizing an oligonucleotide according to the Table 1 protocol with reference to Steps P52 and P58 indicating the repetitive nature of the cycle. In FIG. 5, R' is preferably a 2' protecting group, H, or any other non-reactive group, and the remaining variables are as described in reference to Formula (I).

Figures 6, 6B:
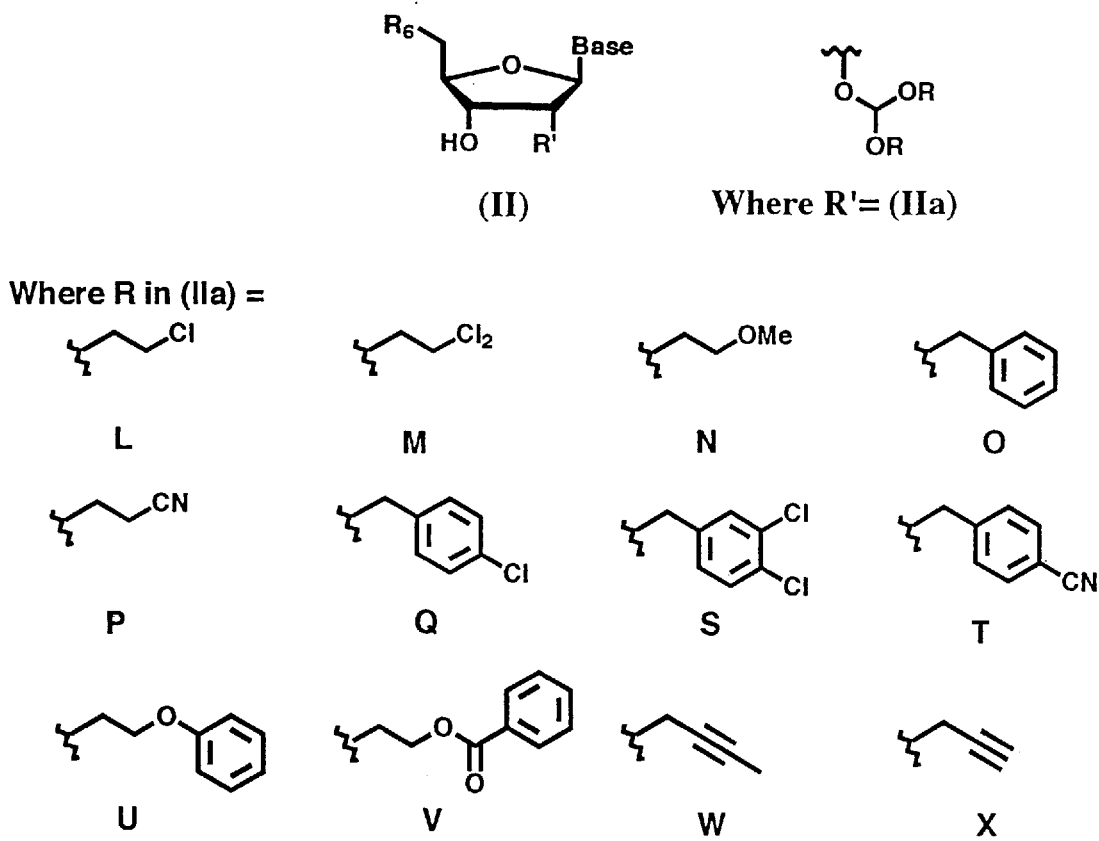
FIG. 6 depicts a figure which represents a 2' protected nucleoside precursor for use in synthesizing RNA according to the present invention.
FIG. 6(B) presents the half-line of synthesized compounds from the various substituents of FIG. 6.
Figure 6A:
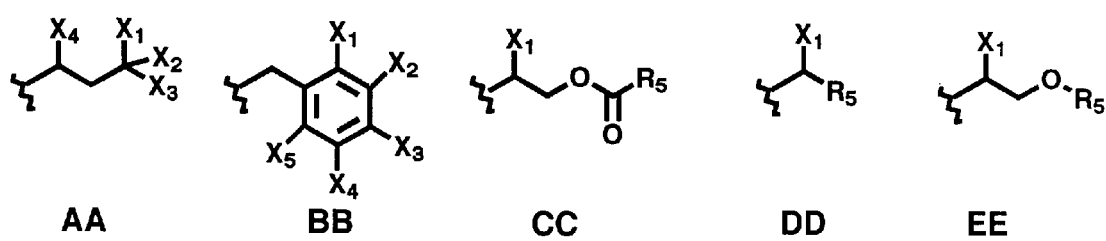
FIG. 6A depicts various substituents for use in combination with the FIG. 6 precursor.

FIG. 6 depicts Formula (II), which represents a 2' protected nucleoside precursor for use in synthesizing RNA. In FIG. 2, the R' is a 2' orthoester group corresponding to R' of Formula (I) (see FIG. 1); BASE' preferably includes a moiety selected from the group consisting of adenine, guanine, cytosine, uracil, or functional homologues thereof, and $R_6$ can be any substituent but preferably is a silyl ether group, hydrogen, hydroxyl, or organic ligand. Formula (IIa) is a particularly preferred noncyclic orthoester for use as R' in Formula (I) and Formula (II). In Formula (IIa), R is preferably one of substituents (AA), (BB), (CC), (DD), and (EE) as shown in FIG. 6A., wherein $X_1$, $X_2$, $X_3$, $X_4$, and $X_5$ can be any compatible ligand, are preferably a hydrogen, halogen, alkyl group, or cyano substituent; and $R_5$ is can be any compatible organic ligand. R' even more preferably comprises Formula (IIa) having as R one of the substituents (L), (M), (N), (O), (P), (Q), (S), (T), (U), (V) and (X). The remaining variables are as described in reference to Formula (I). The broken line attached to each of the substituents (L) through (X) indicates a locus for R group attachment to an oxygen of the 2' orthoester.

All of these substituents were synthesized and tested for viability as R substituents. The major orthoester selection criterion was the stability of ultimate orthoester, i.e. as measured by half life of 2'-O-orthoester uridine in a pH 2 environment. Trials with several orthoesters suggested that the preferred orthoesters required a minimum half life exceeding five minutes in a pH 2 environment at a temperature of 25° C. The pH adjustment was conducted by addition of hydrochloric acid to water.

FIG. 6(B) is presented directly beneath FIG. 6 for easy reference thereto. The first column of FIG. 6(B) includes a description of the synthesized compound, e.g., the first entry describes a compound wherein all R substituents are (L) moieties. The second column of FIG. 6(B) describes the half life of the compound in a pH 2 environment, as determined by HPLC. The compounds of FIG. 6(B) and the substituents of FIG. 6 provide an exemplary list of compounds that form suitable orthoester protecting groups. Those skilled in the art will understand that numerous other suitable compounds exist having similar effect on the basicity of the oxygens in the orthoester. Each orthoester protected nucleoside has different acid lability. 4-N-benzoyl cytidine and uridine are comparable, while 6-N-benzoyl-adenosine and 2-N-isobutyryl-guanosine are both about 3 times more stable. Therefore, the most preferred orthoesters for use in oligonucleotide synthesis were tri-2-butyne orthoester for C and U nucleosides and triphenoxyethyl orthoester for A and G nucleosides.

Figure 7:
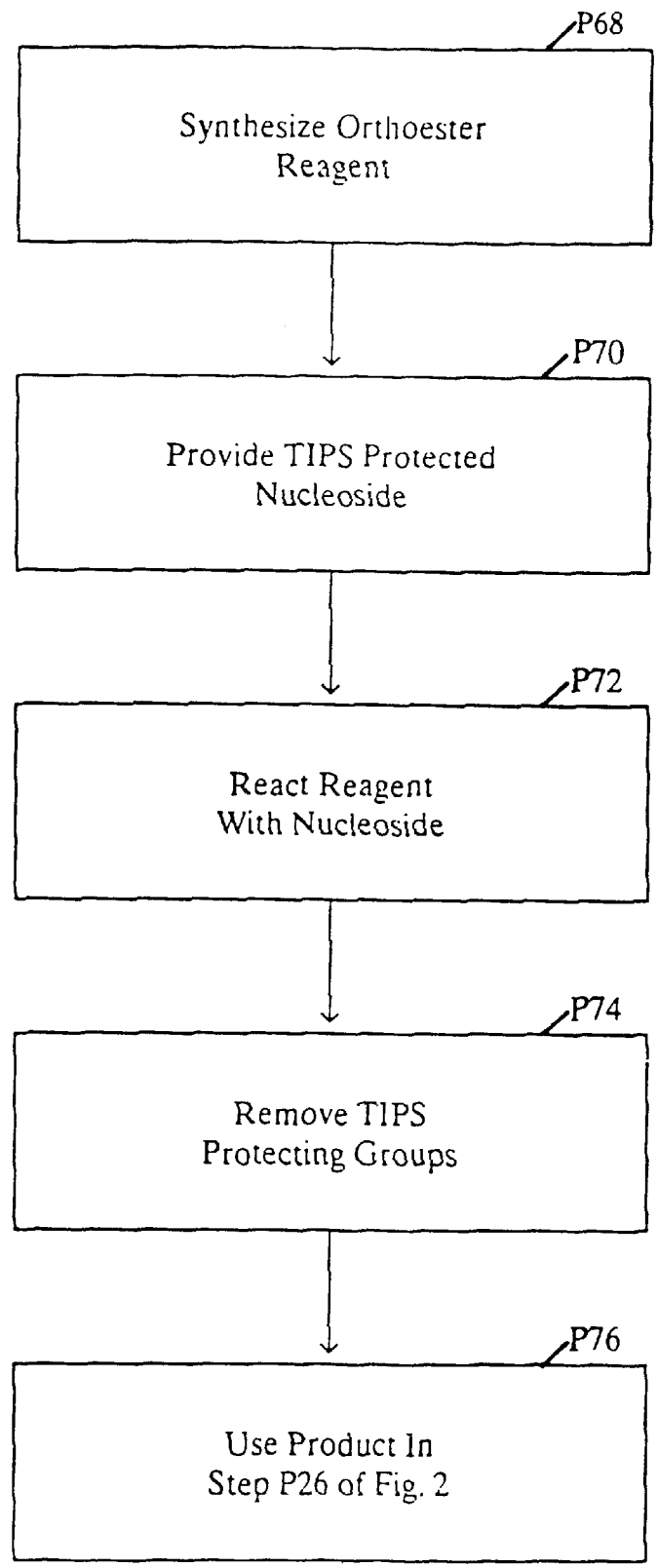
FIG. 7 depicts a schematic process flow diagram for the synthesis of orthoester protected precursors according to the present invention.

FIG. 7 depicts a schematic process flow diagram for the synthesis of orthoester protected precursors according to Formula (II), and the subsequent use of these precursors to obtain the precursor of Formula (I) for application in the process of FIG. 2.

Step P68 includes synthesis of an orthoester reagent. This step preferably includes the reaction of trimethylorthoformate and an alcohol that but for the hydroxy moiety of the alcohol corresponds to the substituents (L) through (X) in FIG. 6. These reagents are preferably combined for reaction in the presence of a catalytic amount of p-toluenesulfonic acid. Methanol is removed during the reaction by distilling at atmospheric pressure and temperatures greater than 100° C. to drive reaction forward.

Step P70 includes providing a ribonucleoside that is protected at the 5' and 3' ribose oxygens. The preferred protected nucleosides are 5',3'-O-tetraisopropylsiloxyl-nucleosides, which may be purchased from Monomer Sciences of Huntsville, Ala. The tetraisopropylsiloxyl moieties are hereinafter referred to as TIPS protecting groups.

Step P72 includes reacting the protected nucleosides of Step P72 with the orthoester reagent of Step P68. Except for uridine nucleosides, the reaction with the preferred TIPS nucleoside is preferably conducted in a dibutylphthalate solvent with high vacuum distillation of the alcohol by product to improve the yields which, otherwise, typically ranges from 20% to 60%. The reaction with uridine nucleosides are best facilitated by using no solvent.

Step P74 includes removal of the 5',3'-TIPS protecting group from the reaction product of Step P72. Removal of the preferred TIPS groups is preferably conducted by reaction with triethylamine-hydorfluoride in acetonitrile.

Step P76 includes use of the reaction product from Step P74 in step P26; of FIG. 2, in order to provide a 2' orthoester-protected phosphoramidite nucleoside in Step P42 of the process depicted in FIG. 4.

EXAMPLE 3

Synthesis of 2' Orthoester Protected Nucleoside Monomers 2'-O-Butyneorthoester Uridine, 2'-O-Butyneorthoester-N-Benzoyl Cytidine, 2'-O-Phenoxyethyl Orthoester-N-Benzoyl Adenosine, and 2'-O-Phenoxyethylorthoester-N-Isobutryl Guanosine An orthoester reagent was synthesized from 2-butene-1-ol. A reaction mixture was prepared including a 2.90 mole quantity (203.3 g) of redistilled 2-butyne-1-ol, a 0.935 mole quantity (102.3 ml) of trimethyl orthoformate (0.935 moles, 102.3 ml), and a catalytic amount (0.018 moles, 4.69 g) of p-toluenesulfonic acid were dissolved in 100 ml dioxane. The dioxane solvent was distilled off under reduced pressure. Four repeat cycles were conducted wherein an additional 150 ml quantity of dioxane solvent was added to the reaction mixture subsequently removed by distillation. A 5 ml quantity of triethylamine was added to the mixture, in order to quench the reaction. The crude reaction product was distilled from the reaction mixture at 95° C. and a vacuum of 10 μm Hg to provide a purified reaction product including a 54% yield of tri(2-butyne)-orthoester.

The resultant orthoester product was used in the synthesis of 2'-O-butyne orthoester uridine. A reaction mixture was mixed to include a 5.11 mmole quantity (2.973 g) of 5'-3'-O-TIPS-uridine, a 0.611 mmole quantity (153 mg) of p-toluene sulfonic acid, and a 30.55 mmole quantity (6.73 g) of tri(2-butyne)-orthoester. The reaction mixture was heated under high vacuum at 65° C. for 3 hours. A 1 ml quantity of triethylamine was added to quench the reaction. The 5',3' TIPS groups was cleaved by the addition of 5 ml 1.0M HF, 2.0M triethylamine in acetonitrile. The cleavage reaction was complete after 1 hour. The solvent was removed in vacuo, and the residue was purified on silica gel to provide a 60.3% yield.

The orthoester product was also utilized in the synthesis of 2'-O-butyneorthoester-4-N-benzoyl cytidine. The procedure was identical to that described in the preceding paragraph, except that 5',3'-O-TIPS-(N-benzoyl)-cytidine was substituted for the 5',3'-O-TIPS-uridine.

A phenoxyethyl orthoester was utilized in the synthesis of 2'-O-phenoxyethanol orthoester-N-benzoyl adenosine. A reaction mixture was prepared to include a 15 mmole quantity (9.2 g) of 5',3'-O-TIPS-(N-benzoyl) adenosine dissolved in 50 ml of dioxane solvent with a 0.75 mmole quantity (188 mg) of p-toluene sulfonic acid and a 45 mmole quantity (19.1 g) of triphenoxyethanol orthoester. The reaction mixture was heated to 65° C. and left to incubate overnight at that temperature. Triethylamine was added to quench the reaction, and the solution was passed over silica gel to remove an excess amount of the orthoester reagent. The collected fractions including the desired reaction product were combined and the solvent was removed in vacua. The 5' and 3' TIPS protecting groups were removed by the addition of a 30 ml solution including 1.0M HF and 2.0M triethylamine in acetonitrile. The yield of the desired reaction product was 19%. 2'-O-phenoxyethylorthoester-N-isobutryl guanosine was prepared by a similar procedure.

EXAMPLE 4

Synthesis of a DNA Homopolymer dT-dT-dT-dT-dT (Sequence ID No. 1)

A synthesis of 3'O-diisopropylmethoxyphosphine-thymidine monomer was conducted as described in Example 1, and used to synthesize a thymidine homopolymer according to the DNA synthesis protocols set forth in Example 2.

Figure 8:
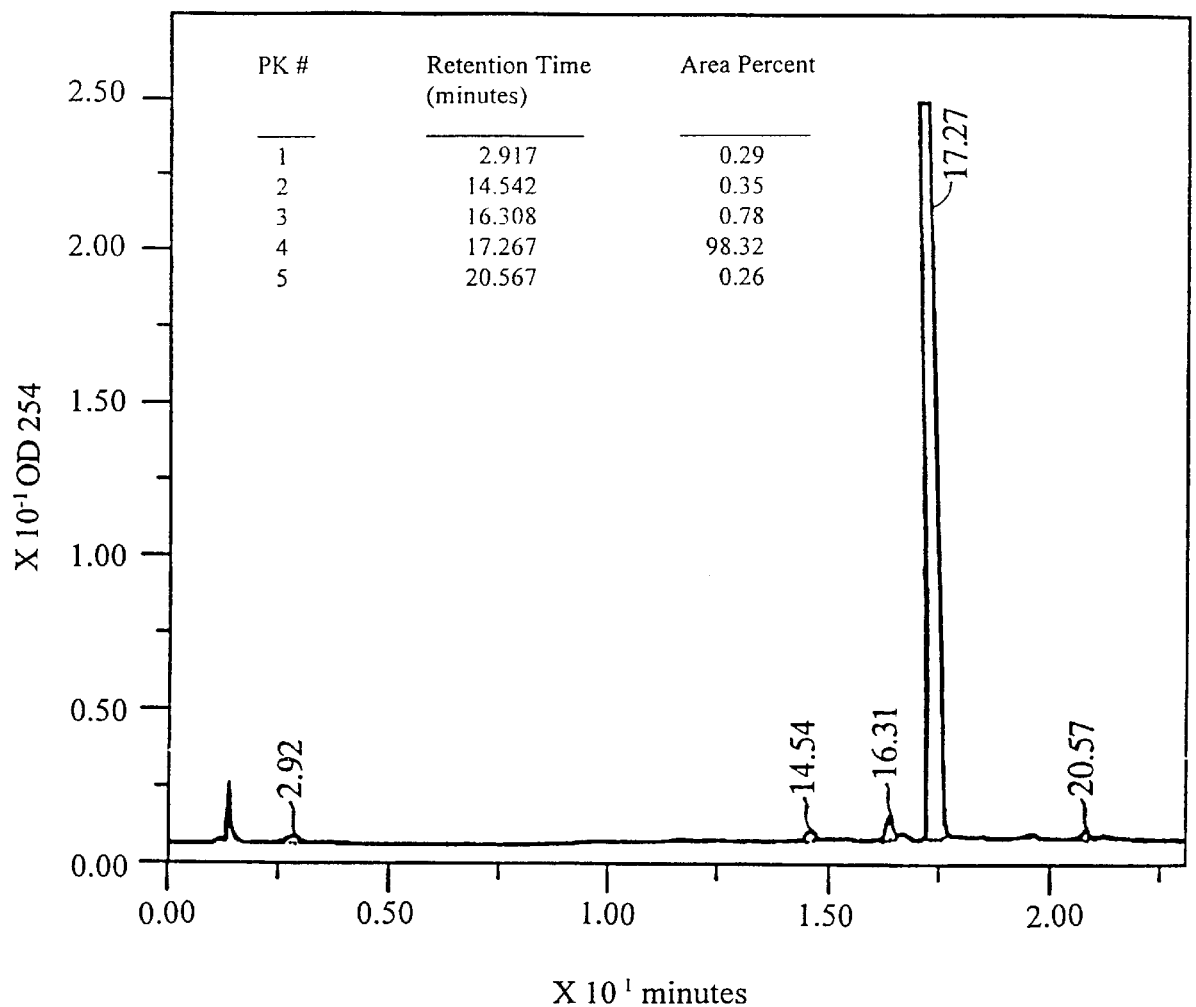
FIG. 8 depicts a high pressure liquid chromatography ("HPLC") trace of a polythymidine reaction product prepared according to the present invention.

FIG. 8 depicts a high pressure liquid chromatography ("HPLC") trace of the reaction products. The X-axis represents time in tenths of minutes. The Y-axis represents a relative spectral absorption at a wavelength of 260 nm. Each peak is labeled with a computer-generated area underlying the peak. The "Area Percent" column identifies a relative abundance of the reaction product associated with each peak. Two significant observations arise from the results depicted in FIG. 8. First, a 98% yield of the full length reaction product is as good as compared to conventional yields for DNA synthesis having more than five connected monomer. Second, there is a diminished relative abundance of longer-retained products at times greater than about 0.15 minutes. The essential absence of these large products simplifies the purification precess.

EXAMPLE 4

Synthesis of a DNA Homopolymer dA-dA-dA-dA-dA-dA-dA-dA-dA-dA-T (Sequence ID No. 2)

The polyadenylated homopolymer sequence corresponding to Sequence ID No. 2 was synthesized by the DNA protocols set forth in Example 2. Comparative results were obtained from the conventional dimethyoxytrityl protocols set forth by ABI of Foster City, Calif.

A silyl protected phosphoramidite adenosine nucleoside monomer was prepared in an identical manner with respect to Example 1, except an N-benzoyldeoxyadenosine nucleoside was substituted for the thymidine nucleoside.

Synthesis and deprotection of the polymer employed conditions identical to those set forth in Example 2. Ammonium hydroxide treatment for cleavage from the support required a five hour reaction time at 65° C. The crude oligonucleotide products were analyzed by ion-exchange HPLC.

Figure 9:
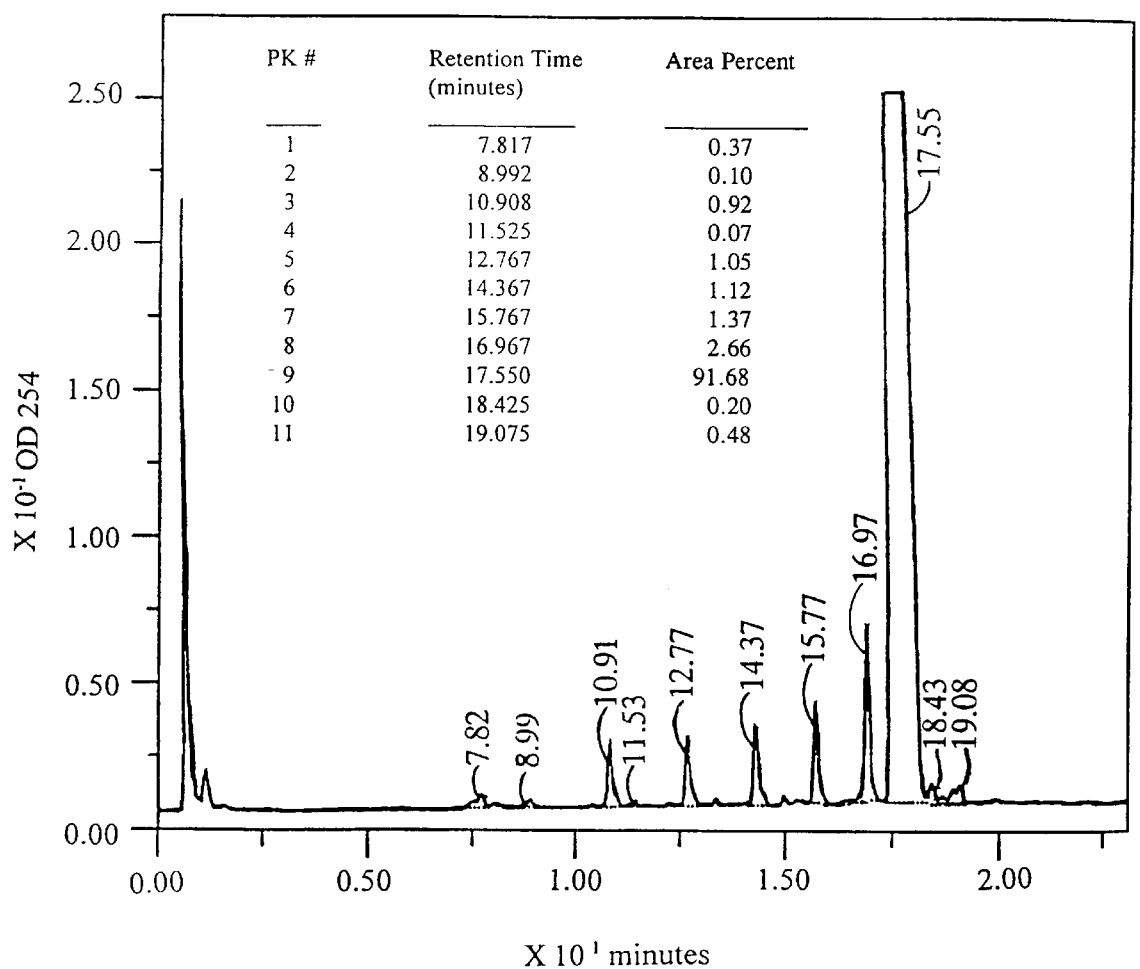
FIG. 9 depicts a HPLC trace similar to that of FIG. 8, but represents results from a polyadenylated sequence.
Figure 10:
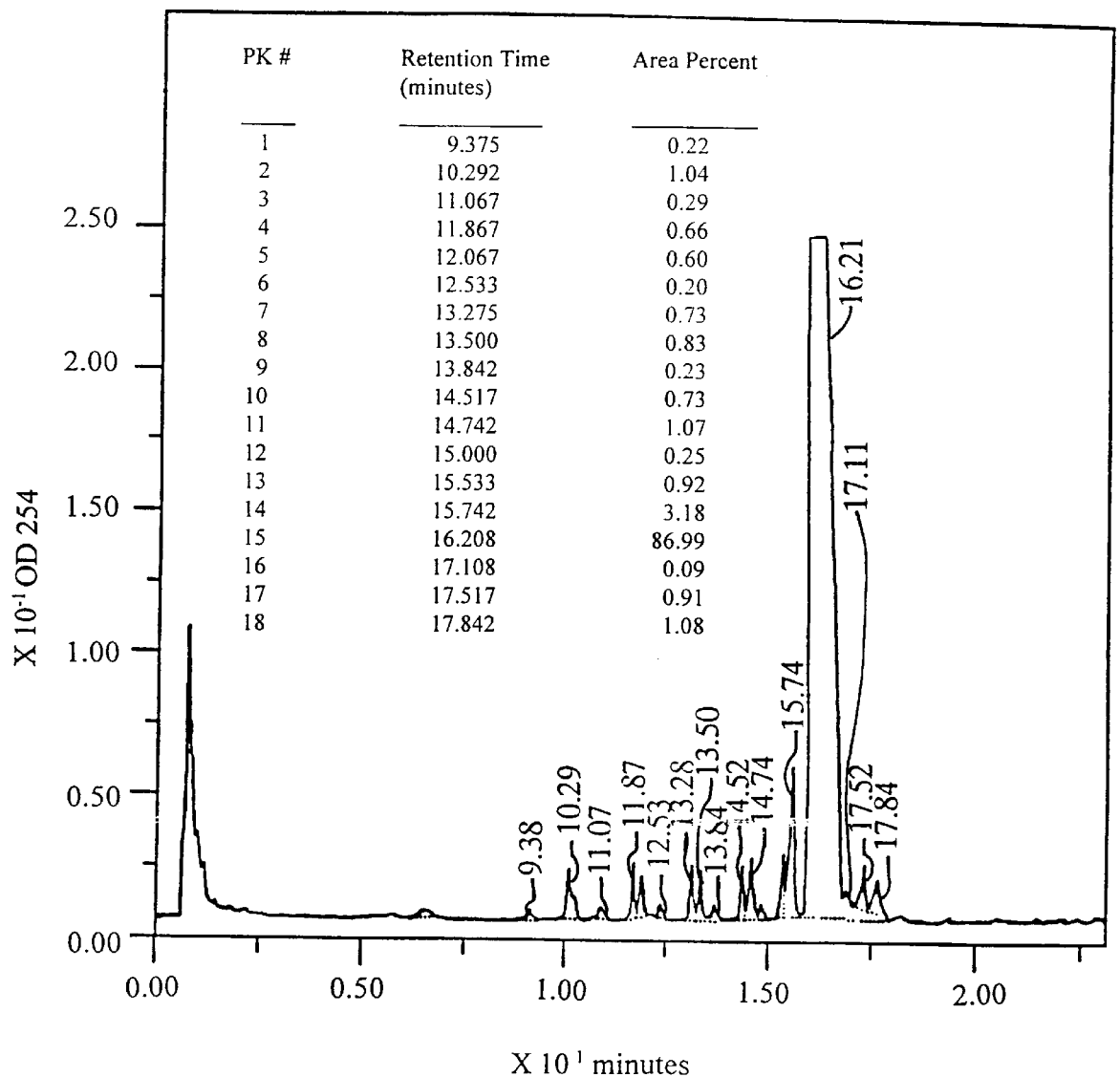
FIG. 10 depicts a trace like that of FIG. 8, but represents results from a polyadenylated sequence prepared according to dimethoxytrityl protecting group chemistry.

FIG. 9 depicts a HPLC trace for the oligonucleotide products that derived from the silyl protected monomers indicating a 92% relative abundance of the full length product and a total 0.68% relative abundance of longer retained impurities. FIG. 10 depicts a comparative HPLC trace of oligonucleotide products that derived from the conventional dimethoxytrityl protocols indicating an 87% relative abundance of the full length product and a 1.99% relative abundance of longer retained impurities.

EXAMPLE 5

Synthesis of Homopolymers of $(rU)_9T$, $(rC)_9T$, $(rA)_9T$

A plurality of 2' orthoester protected RNA nucleoside monomer precursors were synthesized as in Example 3. These precursors included 2'-O-butyne orthoester uridine, 2'-O-butyneorthoester-4-N-benzoyl cytidine, and 2'-O-phenoxyethyl orthoester-N-benzoyl adenosine. A 5'-O-silyl protecting group and ed a 3'-O-diisopropylmethoxyphosphine moiety were added to the respective precursors as in Example 1 to provide monomers for synthesis according to the protocols set forth in Example 2.

Figure 11:
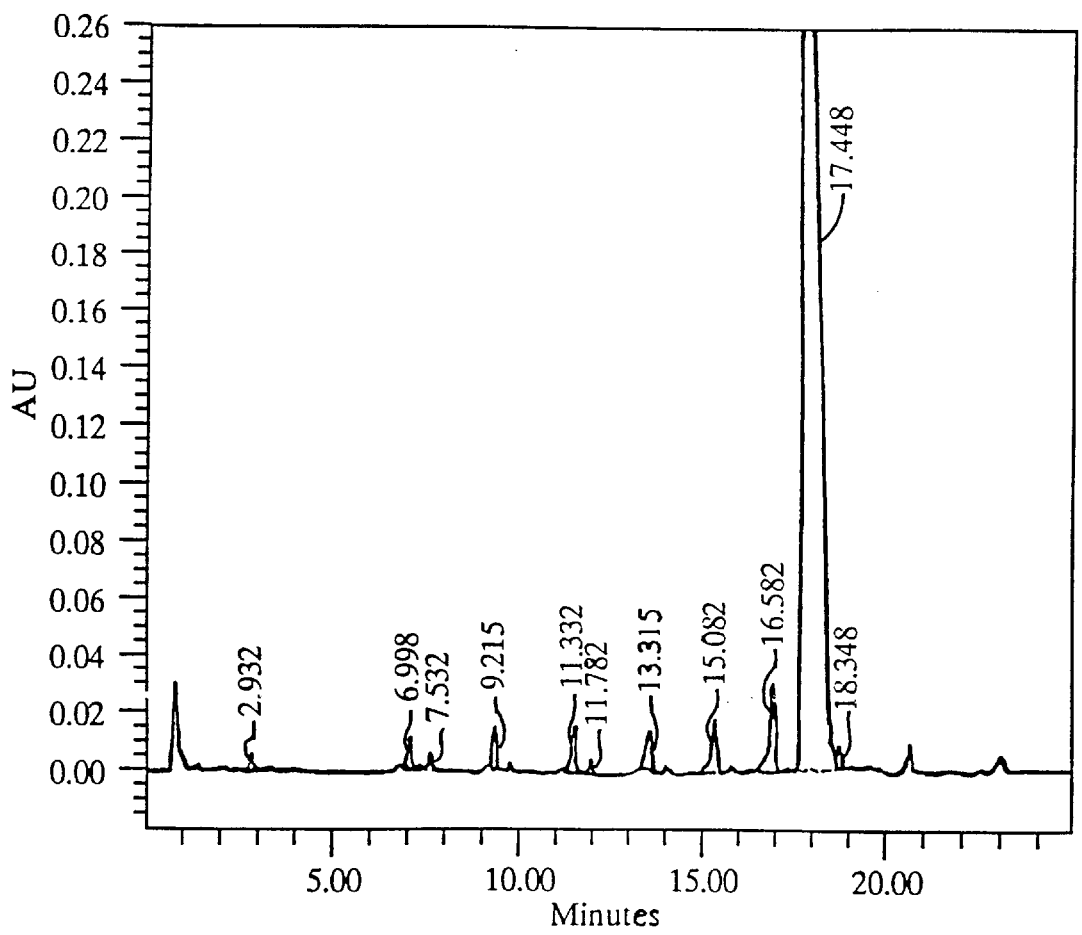
FIG. 11 depicts an HPLC trace similar to that of FIG. 8, but represents results obtained from $(rU)_9T$.
Figure 12:
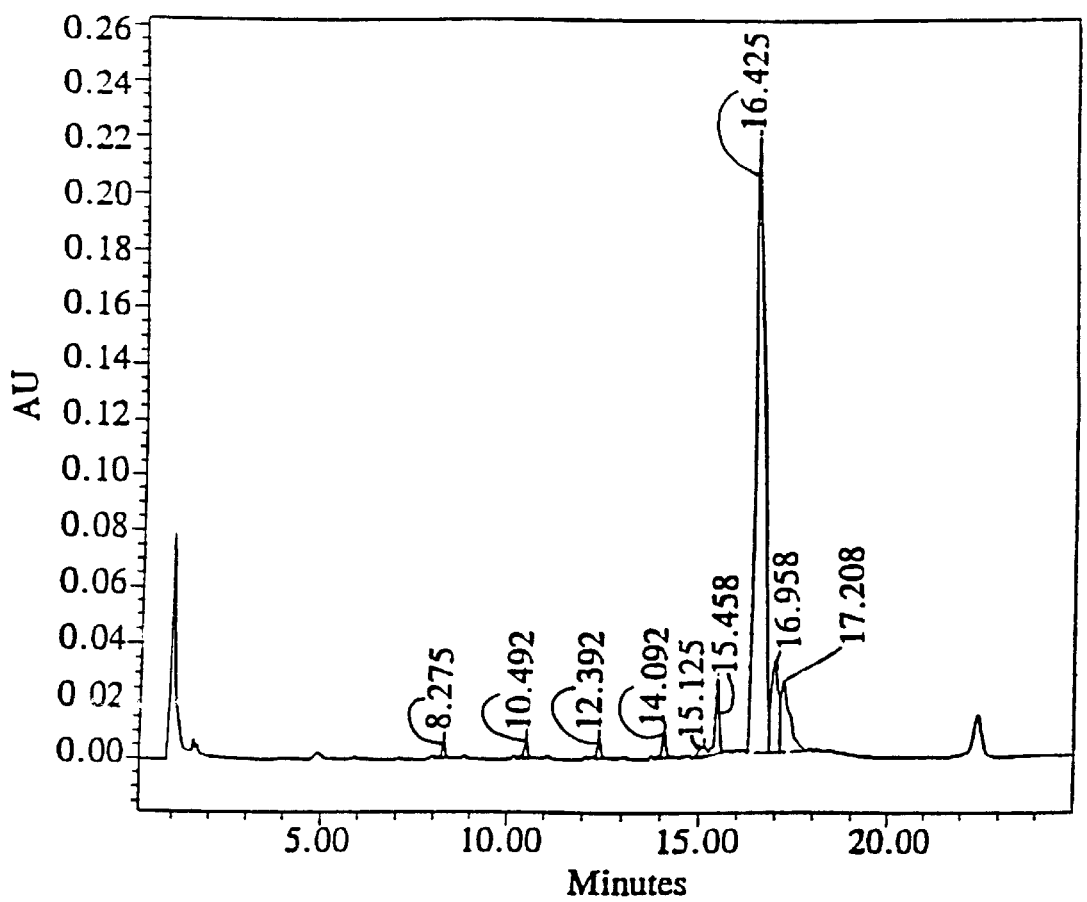
FIG. 12 depicts an HPLC trace similar to that of FIG. 8, but represents results obtained from $(rC)_9T$.
Figure 13:
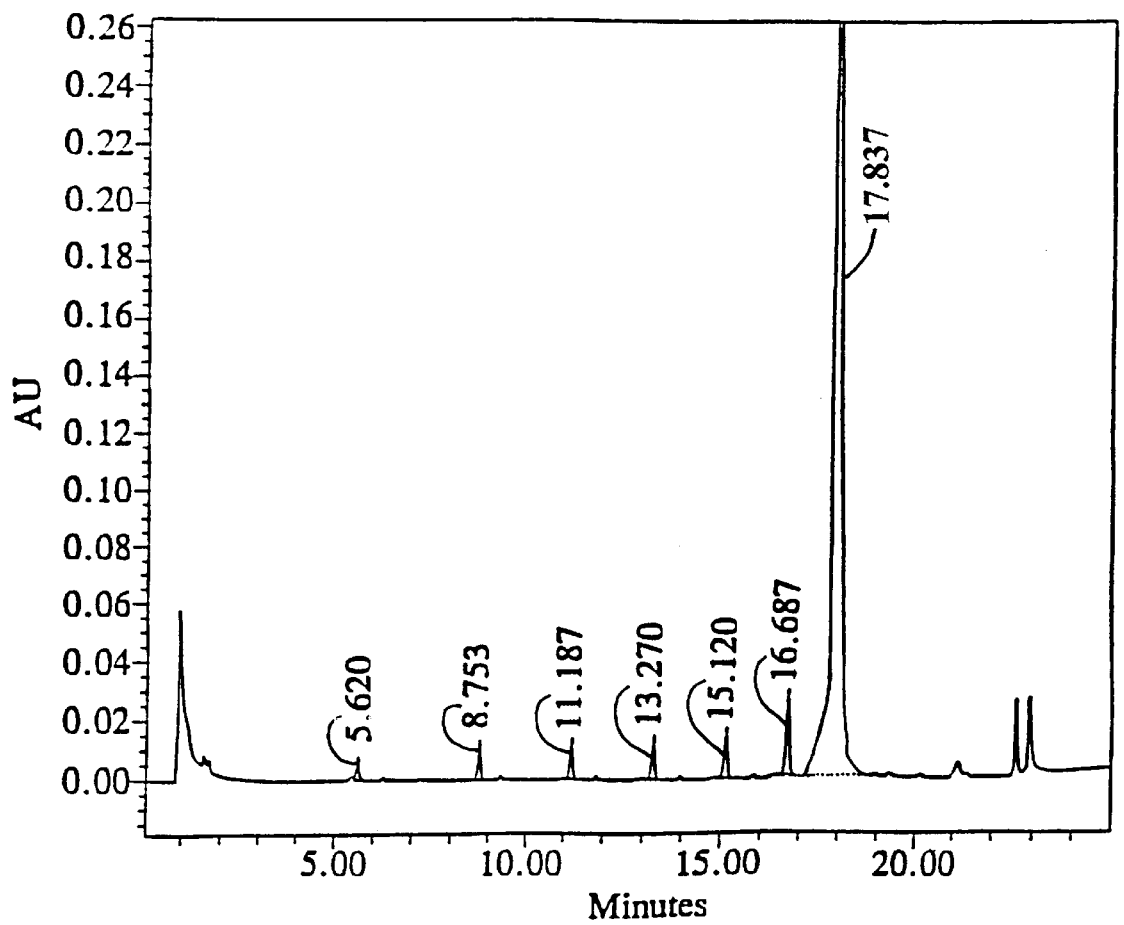
FIG. 13 depicts an HPLC trace similar to that of FIG. 8, but represents results obtained from $(rA)_9T$.
Figure 14:
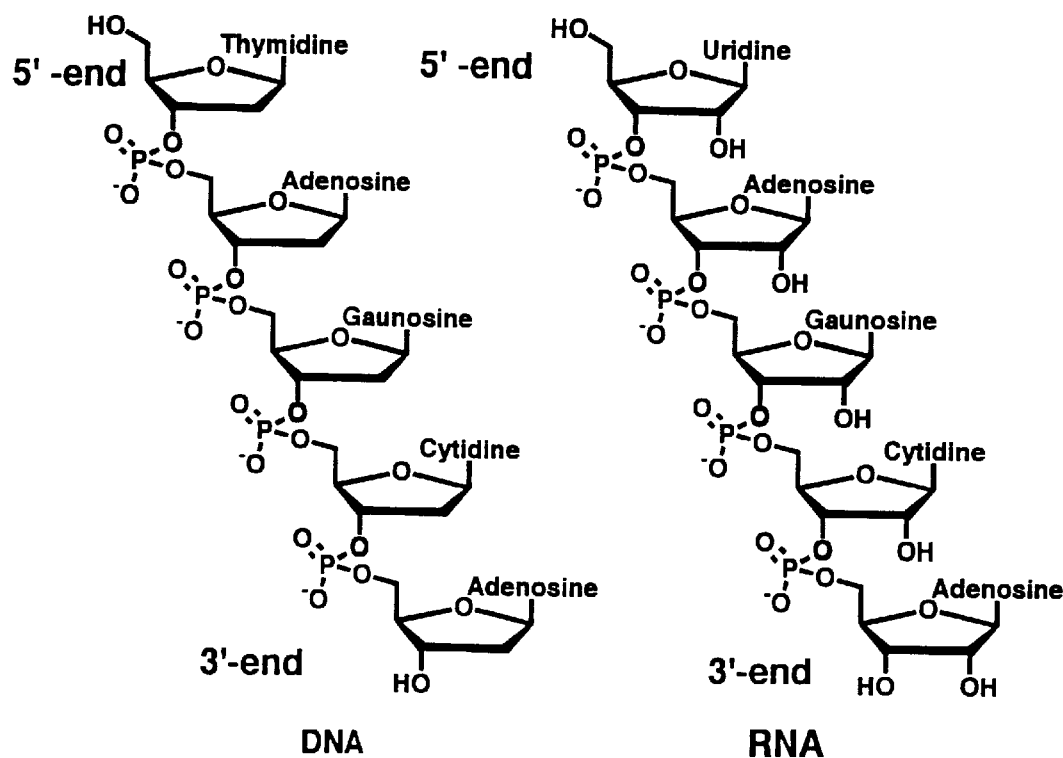
FIG. 14 depicts a DNA chain and an RNA chain each five monomer subunits long and including each of the four naturally occurring deoxyribonucleosides and the four naturally occurring ribonucleosides, the 5' and 3' ends being labelled.
Figure 15:
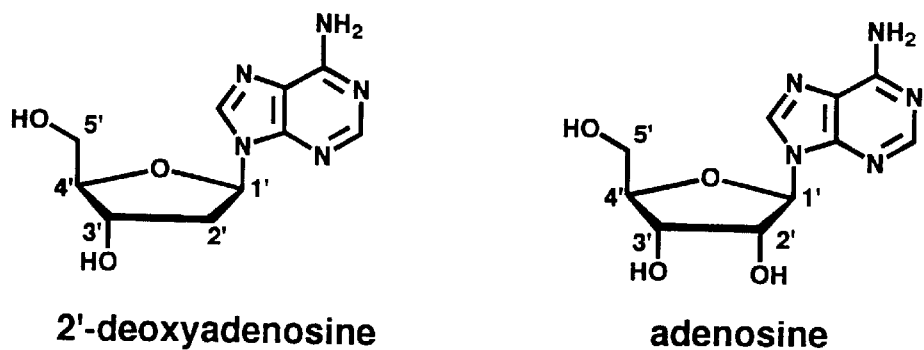
FIG. 15 depicts the structures 2'-deoxyadenosine and riboadenosine and illustrates the numbering of the sugar ring.
Figure 16:
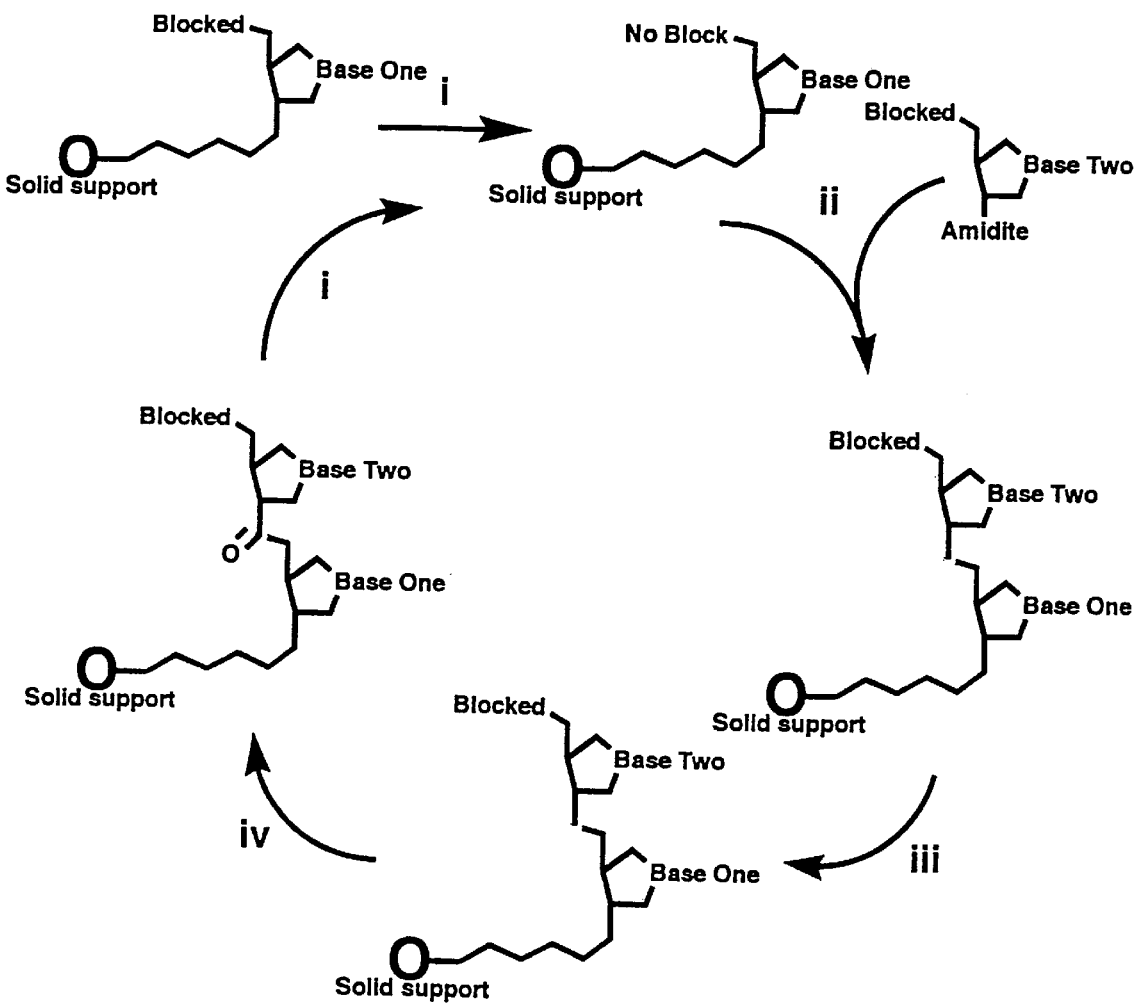
FIG. 16 depicts a schematic representation of the cycle of reactions used in standard oligonucleotide synthesis strategies.

Oligonucleotides including $(rA)_9T$ (Sequence ID No. 3), $(rC)_9T$ (Sequence ID No. 4) and $(rU)_9T$ (Sequence ID No. 5) were synthesized as described in Example 2 with the exception that 0.15M S-ethyl-tetrazole in acetonitrile was used as coupling catalyst. The time allocated to the coupling reaction (Step P58) was, accordingly, extended to four minutes. Deprotection was similar to deoxynucleotide polymers with the exception that thio-salt deprotection time was ) increased to 30 minutes and the $NH_4OH$ contact time extended overnight. The samples were dried to a powder and resuspended in a potassium phosphate buffer (pH 3.0) where they were incubated at 65° C. for one hour. An equal volume of 0.15M tris (pH 8.5) was added and the resultant mixture was heated at 65° C. for 30 minutes. The oligonucleotide products were analyzed by ion exchange HPLC. FIG. 11 depicts the HPLC trace for $(rU)_9T$. FIG. 12 depicts the HPLC trace for $(rC)_9T$. FIG. 13 depicts the HPLC trace for $(rA)_9T$. With the exception of $(rC)_9T$, these traces indicate excellent homopolymer yields.

EXAMPLE 6

Heteropolymer Synthesis With Comparative HPLC Analysis and Ribozyme Cleavage Assay Synthesis and deprotection of heteropolymers was conducted in an identical manner to the RNA synthesis protocols set forth in Example 2. Table 2 serves to identify the various heteropolymer sequences that were synthesized. Sequence ID No. 6 is a substrate template for ribozyme cleavage. Sequence ID No. 9 is a corresponding ribozyme sequence. Sequence ID No. 7 is a mixed polymer. Sequence ID No. 8 is the same as Sequence ID No. 7 with cytidine replaced by uridine.

TABLE 2

HETEROPOLYMER SEQUENCES

| Sequence ID No. | Sequence |
| --- | --- |
| 6 | 5'-GAAUCGAAACGCGAAAGCGUACUAGCG-T-3' |
| 7 | 5'-CUUAGAGUAGUCAUCGC-T-3' |
| 8 | 5'-UUUAGAGUAGUUAUUGU-T-3' |
| 9 | 5'-CGCUACUGAUGAGAUUC-T-3' |

The #6 sequence and corresponding ribozyme sequence #9 were synthesized by dimethoxytrityl chemistry using standard protocols set forth by ABI of Foster City, Calif. Sequence #9 includes the same length and base composition as sequence #7, but arranged in a different sequential order. Ion exchange HPLC analysis of crude oligonucleotides yielded the following results in Table 3. Overall crude product yields were significantly more for oligonucleotides synthesized via this invention. Table 3 facilitates a comparative analysis of the full length product yields that derive from silyl protecting group chemistry versus analogous yields from the conventional dimethoxytrityl protecting group chemistry.

TABLE 3

COMPARISON OF OLIGONUCLEOSIDE YIELDS BETWEEN SILYL PROTECTING GROUP PROTOCOLS AND CONVENTIONAL PHOSPHORAMIDITE PROTOCOLS

| Sequence ID No. | Dimethoxytrityl Chemistry | Silyl Chemistry |
| --- | --- | --- |
| 6 | 45% | 37% |
| 7 |  | 72% |
| 8 |  | 75% |
| 9 | 62% |  |

Table 3. Comparison of percent of full length product in crude synthesis

Oligonucleotides corresponding to Sequence Nos. 6 were synthesized by both methods. The respective oligonucleotide products were purified by HPLC. Both of the #6 sequences were labelled with $P^{32}$ via kinase reaction according to conventional protocols, and incubated with the No. 9 sequence. Time points were generated on polyacrylamide gel electrophoresis ("PAGE") to analyze the rate and extent to which the No. 6 sequences incurred cleavage. Table 4 includes the PAGE results.

TABLE 4

COMPARISON OF KINETIC DATA FOR CLEAVAGE OF RIBOZYME SUBSTRATE

|  | Dimethoxytrityl Chemistry | Silyl Chemistry |
| --- | --- | --- |
| % Substrate Uncleaved | 17% | 18% |
| Initial Rate | 0.703 $min^{-1}$ | 0.831 $min^{-1}$ |

Those skilled in the art will understand that the above discussion serves to identify preferred methods and materials for use in the present invention. The preferred embodiments, as described hereinabove, may be subjected to apparent modifications without venting from the true scope and spirit of the invention. Accordingly, the inventors hereby declare their intention to rely upon the Doctrine of Equivalents, in order to protect their full rights in the invention.

---

We claim:

1. An orthoester reagent for use as a protecting group having the formula:

R₁O\C(OR₂)/OR₃ wherein $R_1$, $R_2$ and $R_3$, independently of one another, are selected from the group

[structures: -CH₂CH₂CHCl₂, -CH₂CH₂CH₂Cl, -CH₂CH₂CN,
-CH₂CH₂CH₂OMe, -CH₂-C₆H₄-Cl, -CH₂-C₆H₄-CN, -CH₂CH₂CH₂OC(O)Ph, -CH₂C≡CH, -CH₂CH₂C≡CH, -CH₂CH₂CH₂OPh, -CH₂-C₆H₃(Cl)(Cl)],

[structures with X₁, R₅; X₄, X₁, X₂, X₃; X₁, OC(O)R₅; benzyl; X₁, X₂, X₃, X₄, X₅ on phenyl; X₁, OR₅]

wherein $X_1$, $X_2$, $X_3$, $X_4$ and $X_5$ are, independently of one another, a hydrogen, a halogen, an alkyl group, a cyano group or a compatible ligand, and wherein $R_5$ is an organic ligand.

2. The orthoester reagent of claim 1, wherein $R_1$, $R_2$ and $R_3$ are selected from the group

[structures: -CH₂CH₂CHCl₂, -CH₂CH₂CH₂Cl, -CH₂CH₂CN, -CH₂CH₂CH₂OMe, -CH₂-C₆H₄-Cl, -CH₂-C₆H₄-CN, -CH₂CH₂CH₂OC(O)Ph, -CH₂C≡CH, -CH₂CH₂C≡CH, -CH₂CH₂CH₂OPh, -CH₂-C₆H₃(Cl)(Cl), and benzyl].

3. The orthoester reagent of claim 1, wherein $R_1$ equals $R_2$.

4. The orthoester reagent of claim 1, wherein $R_1$ and $R_2$ are alkyl groups.

5. The orthoester reagent of claim 4, wherein said alkyl groups are alkynyl groups.

6. The orthoester reagent of claim 5, wherein $R_1$ and $R_2$ are 2-butynyl groups.

7. The orthoester reagent of claim 1, wherein $R_1$, $R_2$ and $R_3$ are 2-butynyl groups.

8. The orthoester reagent of claim 1, wherein $R_1$ and $R_2$ are phenoxyethyl groups.

9. The orthoester reagent of claim 1, wherein $R_1$, $R_2$ and $R_3$ are phenoxyethyl groups.

10. A method for making an orthoester reagent of claim 1, comprising the steps of:

mixing trimethylorthoformate and an alcohol in a solvent to produce a reaction mixture, and removing said solvent from the reaction mixture to yield said orthoester reagent.

11. The method of claim 9, wherein said alcohol is 2-butyne-1-ol.

12. The method of claim 9, wherein said alcohol is phenoxyethanol.

13. The method of claim 9, wherein said solvent is dioxane.

14. The method of claim 10, wherein said catalyst is p-toluenesulfonic acid.

15. The method of claim 9, further comprising a reaction quenching step, wherein said reaction quenching step comprises adding triethylamine to the reaction mixture.

* * * * *